US006268180B1

(12) United States Patent
Gubler et al.

(10) Patent No.: US 6,268,180 B1
(45) Date of Patent: Jul. 31, 2001

(54) RECOMBINANT HUMAN RECOMBINANT HUMAN INTERLEUKIN-1α

(75) Inventors: Ulrich A. Gubler, Glen Ridge, NJ (US); Peter T. Lomedico, Waltham, MA (US); Steven B. Mizel, Lewisville, NC (US)

(73) Assignees: Hoffmann-La Roche Inc., Nutley, NJ (US); The Pennsylvania State University, Park, PA (US)

( * ) Notice: Subject to any disclaimer, the term of this patent is extended or adjusted under 35 U.S.C. 154(b) by 0 days.

(21) Appl. No.: 09/290,563

(22) Filed: Apr. 13, 1999

Related U.S. Application Data

(62) Division of application No. 08/259,927, filed on Jun. 15, 1994, now Pat. No. 5,936,066, which is a continuation of application No. 07/028,429, filed on Mar. 20, 1987, now abandoned, which is a continuation of application No. 06/748,632, filed on Jun. 24, 1985, now abandoned, which is a continuation-in-part of application No. 06/720,774, filed on Apr. 25, 1985, now abandoned.

(51) Int. Cl.[7] .................................................. C12P 21/02

(52) U.S. Cl. .................. 435/69.52; 435/325; 435/252.3; 435/252.33; 536/23.1; 536/23.5

(58) Field of Search .......................... 530/351; 536/23.5, 536/23.1; 435/69.52, 317.1, 325, 252.3–252.35; 514/12

(56) References Cited

U.S. PATENT DOCUMENTS

| | | | |
|---|---|---|---|
| 4,342,832 | 8/1982 | Goeddel et al. | 435/91.41 |
| 4,406,830 | 9/1983 | Fabricius et al. | 530/380 |
| 4,411,992 | 10/1983 | Gillis | 435/70.4 |
| 4,503,035 | 3/1985 | Pestka et al. | 424/85.7 |
| 4,508,833 | 4/1985 | Sonneborn et al. | 530/351 |
| 4,518,584 | 5/1985 | Mark et al. | 424/85.2 |
| 4,711,842 | 12/1987 | Taniyama et al. | 435/70.2 |
| 4,762,914 | 8/1988 | Auron et al. | 530/351 |

FOREIGN PATENT DOCUMENTS

| | | |
|---|---|---|
| 0 092 163 A2 | 10/1983 | (EP) . |
| 0 114 506 A1 | 8/1984 | (EP) . |
| 0 161 901 A2 | 12/1985 | (EP) . |
| 0 165 654 A2 | 12/1985 | (EP) . |
| 0 188 864 A1 | 7/1986 | (EP) . |
| 0 188 920 A2 | 7/1986 | (EP) . |
| 0 200 986 A1 | 11/1986 | (EP) . |
| 2 063 882 | 6/1981 | (GB) . |
| 59-278665 | 12/1984 | (JP) . |
| 60-39762 | 2/1985 | (JP) . |
| 60-112474 | 5/1985 | (JP) . |
| 60-171493 | 8/1985 | (JP) . |
| 60-200894 | 9/1985 | (JP) . |

OTHER PUBLICATIONS

Oppenheim et al., 1986, There is more than one interleukin 1, Immunology Today 7(2):45–57.

Dukovich et al., 1986, Stimulation of fibroblast proliferation and prostaglandin production by purified recombinant murine interleukin 1, Clin Immunol and Immunopathol 38:381–389.

Lomedico et al., 1986, Molecular biology of interleukin–1, Cold Spring Harbor Symposia on Quantitative Biology, vol. LI, pp. 631–639.

Tsunasawa et al, 1985, Amino terminal processing of mutant forms of yeast ISO–1–cytochrome c, J Biol Chem 260(9):5382–5391.

Kronheim et al., 1985, Human interleukin 1: purification to homogeneity, J Exp Med 161:490–502.

Wood et al., 1985, The four biochemically distinct species of human interleukin 1 all exhibit similar biologic activities, J Immunol 134(2):895–903.

Auron et al., 1985, Human and Murine Interleukin 1 Possess Sequence and Structural Similarities, J. Mol. Cell. Immunol. 2:169–177.

Krakauer, 1985, Purification to homogeneity of biologically active human interleukin 1, Chemical Abstracts v102 p457 abstract 219322q.

Prestidge, 1985, Partial characterization of the high and low molecular weight forms of P388D1–derived interleukin 1, Chemical Abstracts v102, p446, abstract 77013p.

Saklatvala et al., 1985, Pig Interleukin 1, J. Exp. Med. 162:1208–1222.

March et al., 1985, Cloning, sequence and expression of two distinct human interleukin–1 complementary DNAs, Nature 315(6021):641–647.

Cameron et al., 1985, Amino acid sequence analysis of human interleukin 1 (IL–1): evidence for biochemically distinct forms of IL–1, J Exp Med 162:790–801.

Sherman et al., 1985, Methionine or not methionine at the beginning of a protein, Bioessays 3(1):27–31.

Furutani et al., 1985, Cloning and characterization of the cDNAs for human and rabbit interleukin–1 precursor, Nucleic Acids Research 13(16):5869–5882.

Matsushima et al., 1985, Purification of human interleukin 1 from human monocyte culture supernatants and identity of thymocyte comitogenic factor, fibroblast–proliferation factor, acute–phase protein–inducing factor, and endogenous pyrogen, Cellular Immunology 92:290–301.

1985, Points to Consider in the Production and Testing of New Drugs and Biologicals Produced by Recombinant DNA Technology, Office of Biologics Research and Review Center for Drugs and Biologics.

(List continued on next page.)

Primary Examiner—James Martinell
(74) Attorney, Agent, or Firm—Pennie & Edmonds LLP

(57) ABSTRACT

The invention relates to the cloning of the human interleukin-1α gene, its engineering into suitable expression vectors, hosts transformed with such expression vectors, and production of biologically active recombinant human interleukin-1α.

21 Claims, 9 Drawing Sheets

OTHER PUBLICATIONS

1985, Million Dollar Directory, Series 1985, Dun's Marketing Services, ISSN 0734–2861.

1985, Interleukin–1 Genes Are Cloned, Science 228:1076–1077.

Kurt–Jones et al., 1985, Identification of a membrane–associated interleukin 1 in macrophages, Proc Nat Acad Sci USA 82:1204–1208.

Giri et al., 1985, Studies on the synthesis and secretion of interleukin 1, Journal of Immunology, vol 134(1):343–349.

Mosley et al., 1985, The cloning and expression of two distinct human interleukin–1 (IL–1) cDNAs Progress in Leukocyte Biology 2:521–532. Progress in Leukocyte Biology, Sherwood M. Reichard, ed., Alan R. Liss, Inc., New York, pp. 521–532.

Sahasrabuddhe et al., 1985, Intracellular Human IL–1: A precursor for the secreted monokine, Lymphokine Research 4(3):205–213.

Durum et al., 1985, Interleukin 1: An immunological perspective, Ann. Rev. Immunology 3:263–287.

Dinarello, C.A., 1985, An update on human interleukin–1: From molecular biology to clinical relevance, Journal of Clinical Immunology 5(5):287–297.

Krakauer, 1984–85, Purification to homogeneity of biologically active human interleukin 1, Preparative Biochem 14(5): 449–470.

Auron et al., 1984, Nucleotide sequence of human monocyte interleukin 1 precursor cDNA, Proc. Natl. Acad. Sci. U.S.A. 81:7907–7911.

Auron et al., 1984, Molecular cloning of human interleukin–1, Lymphokine Research 3:285.

Schmidt, J.A., 1984, Purification and partial biochemical characterization of normal human interleukin 1, J. Exp. Med. 160:772–787.

Dinarello, 1984, Interleukin–1, Review of Infectious Diseases 6(1):51–95.

Devereux et al., 1984, A comprehensive set of sequence analysis program for the VAX, Nucleic Acids Res 12(1):387–395.

Morinaga et al., 1984, Improvement of Oligonucleotide–Directed Site–Specific Mutagenesis Using Double–Stranded Plasmid DNA, Bio/technology pp. 636–639.

Matsushima et al., 1984, purification of human interleukin 1 and identity of thymocyte co–mitogenic factor, fibroblast proliferation factor and acute phase protein inducing factor, Fourth International Lympho. Workshop—Molecular and Cellular Biology of Lympho. Abstract p. 259.

Windle et al., 1984, Induction of interleukin 1 messenger RNA and translation in oocytes, J Immunology 132(3):1317–1322.

Dinarello, 1984, Interleukin–1 and the Pathogenesis of the Acute–Phase Response, New England J. of Med. 311:1413–1419.

Dayer et al., 1984, Induction of human interleukin 1 MRNA measured by collagenase– and prostaglandin E2–stimulating activity in rheumatoid synovial cells, Eur. J. Immunol. 14:898–901.

1984, Therapeutic control of inflammatory disease, Program of events—2nd International Conf. Inflammation Research Association.

Lomedico et al., 1984, Cloning and expression of murine interleukin–1 cDNA in Escherichia coli, Nature 312(5993):458–462.

1984, Human IL–1 gene cloning spawns counter–claims, Biotechnology Newswatch Monday Nov. 19, 1984 p. 2 (McGraw Hill).

Kock and Luger, 1984, Purification of human interleukin 1 by high–performance liquid chromatography, J Chromatography 296:293–300.

Scala et al., 1984, Human Large Granular Lymphocytes Are Potent Produces of Interleukin–1, Nature 309:56–59.

Dinarello et al., 1984, Cleavage of human interleukin 1: isolation of a peptide fragment from plasma of febrile humans and activated monocytes, J Immunology 133(3):1332–1338.

Alberts et al., 1983, The Immune System, Molecular biology of the cell, p. 1006.

Lachman, 1983, Human interleukin 1: purification and properties, FASEB J 42(9):2639–2645 (Fed. Proc.).

Yip, 1983, Stimulation of lymphokine production by teleocidin, aplysiatoxin and debromoaplysiatoxin, Chem Abstracts 99(9):466 No. 68697g.

Gross and Meienhofer, eds., 1983, Synthesis of polypeptides by recombinant DNA methods, The Peptides, pp. 39–41.

Gubler and Hoffman, 1983, Simple and very efficient method for generating cDNA libraries, Gene 25(2–3):263–269.

Mizel et al., 1983, Preparation of Goat Antibodies Against Interleukin–1: Use of an Immunoadsorbent to Purify Interleukin 1, J Immunol 131:1834–1837.

Beltz et al., 1983, Isolation of Multigene Families and Determination of Homologies by Filter Hybridization Methods, Methods Enzymol 100:266–285.

Krakauer and Oppenheim, 1983, Interleukin 1 production by a human acute monocytic leukemia cell line, Cellular Immunology 80:223–229.

Hanahan, 1983, Studies on transformation of Escherichia coli with plasmids, J Mol Biol 166:557–580.

Yip, 1983, Stimulation of lymphokine production by teleocidin, aplysiatoxin and debromoaplysiatoxin, Cell Immunol 79(2):389–395.

Alberts et al., 1983, Recombinant DNA Technology, Molecular Biology of The Cell, Garland Publishing, NY, pp. 185–196.

Di Sabato, 1982, Purification and initial characterization of rat interleukin 2, Proc Nat Acad Sci USA 79(9):3020–3023.

Schmidt et al., 1982, Interleukin 1, a potential regulator of fibroblast proliferation, J Immunol 128:2177–2182.

Acuto et al., 1982, An efficient method for purification of human T–cell growth factor, J Immunol Met 53:15–26.

Welte et al., 1982, Purification of human interleukin 2 to apparent homogeneity and its molecular heterogeneity, J Exp Med 156:454–464.

Dempsey et al., 1982, The differential effect of human leukocytic pyrogen/lymphocyte–activating factor, T cell growth factor, and interferon on human natural killer activity, J Immunology 129(6):2504–2510.

Lachman, Postlethwaite, Gillis, 1982, FASEB 1982: The Year of the Lymphokines 1) (Lachman) Summary of the FASEB symposium on lymphokines and the control of cell growth 2) (Gillis) Summary of FASEB minisymposium on regulation of connective tissue cells by immune and inflammatory cells, Lymphokine Research 1(2).

Gillis, 1982, Biochemical and biological characterization of murine and human interleukin 2, Fed. Proc. 41(3): Abstract 1221.

Olson et al., 1981, Purified human growth hormone from E. coli is biologically active, Nature 293:408–411.

Shepard et al., 1981, A single amino acid change in IFN–b1 abolishes its antiviral activity, Nature 294:563–565.

Mizel and Mizel, 1981, Purification to apparent homogeneity of murine interleukin 1, Journal of Immunology 126(3):834–837.

Parnes et al., 1981, Mouse β2–microglobulin cDNA clones: a screening procedure for cDNA clones corresponding to rare mRNAs, Proc Nat Acad Sci 78(4):2253–2257.

Land et al., 1981, 5' terminal sequences can be cloned with high efficiency, Nucleic Acids Res 9(10):2251–2266.

Fritsch et al., 1980, Molecular Cloning and Characterization of the Human β–like Globin Gene Cluster, Cell 19:959–972.

Lachman et al., 1980, Purification of human interleukin 1, Journal of Supramolecular Structure 13:457–466.

Wallace et al., 1980, Directed deletion of a yeast transfer RNA intervening sequence., Science 209:1396–1400.

Mizel, 1979, Physicochemical characterization of lymphocyte activating factor (LAF), J Immunol 122(6):2167–2172.

Togawa et al., 1979, Characterization of lymphocyte–activating factor (LAF) produced by human mononuclear cells: biochemical relationship of high and low molecular weight forms of LAF, J Immunology 122(5):2112–2118.

Chirgwin et al., 1979, Isolation of biologically active ribonucleic acid from sources enriched in ribonuclease, Biochemistry 18(24):5294–5299.

Koren et al., 1979, In Vitro Activation of a Human Macrophage–like Cell Line, Nature 279:328–330.

Togawa et al., 1979, J Immunol 122:2112–2118.

Goeddel et al., 1979, Expression in Escherichia coli of chemically synthesized genes for human insulin, Biochemistry 76(1):106–110.

Goeddel et al., 1979, Direct expression in Escherichia coli of a DNA sequence coding for human growth hormone, Nature 281(5732):544–548.

Ricciardi, et al., 1979, Purification and mapping of specific mRNAs by hybridization–selection and cell–free translation, Proc. Natl. Acad. Sci. USA 76(10):4927–4931.

Mizel et al., 1978, Characterization of lymphocyte–activating factor (LAF) produced by a macrophage cell line, P388D1. II. Biochemical characterization of LAF produced by activated T cells and LPS, J Immunology 120(5):1504–1508.

Gillis et al., 1978, T cell growth factor: parameters for production and a quantitative microassay for activity, J Immunology 120(6):2027–2032.

Lachman et al., 1977, Partial purification of human lymphocyte–activating factor (LAF) by ultrafiltration and electrophoretic techniques, J Immunol 119(6):2019–2023.

1977, Science 196, Table of Contents No. 4285–4289.

Blyden and Handschumacher, 1977, Purification and properties of human lymphocyte activating factor, J Immunol 118(5):1631–1638.

Smith and Birnstiel, 1976, A simple method for DNA restriction site mapping, Nuc Acid Res 3(9):2387–2398.

Palmiter, 1973, Albumin messenger ribonucleic acid translation, J Biol Chem 6:2095–2106.

Aviv and Leder, 1972, Purification of biologically active globin messenger RNA by chromatography on oligothymidylic acid–cellulose, Proc Nat Acad Sci USA 69(6):1408–1410.

Gery, 1972, Potentiation of the T–lymphocyte response to mitogens. I. The responding cell, J Exp Med 136(1):128–142.

Epstein et al., 1963, The genetic control of tertiary protein structure: Studies with model systems, Cold Spring Harbor Symposium on Quantitative Biology, vol. 28 pp. 439–449.

FIG. 1A

| | |
|---|---:|
| AAG TCT CCA GGG CAG AGA GGG AGT CAA CTC ATT GGC GCT TGA GTC GGC AAA GAA | 54 |
| ATC AAG ATG GCC AAA GTT CCT GAC TTG TTT GAA GAC CTA AAG AAC TGT TAC AGT<br>          MET Ala Lys Val Pro Asp Leu Phe Glu Asp Leu Lys Asn Cys Tyr Ser<br>                                                      10 | 108 |
| GAA AAC GAA GAC TAC AGT TCT GCC ATT GAC CAT CTC TCT CTG AAT CAG AAA TCC<br>Glu Asn Glu Asp Tyr Ser Ser Ala Ile Asp His Leu Ser Leu Asn Gln Lys Ser<br>               20                                          30 | 162 |
| TTC TAT GAT GCA AGC TAT GGC TCA CTT CAT GAG ACT TGC ACA GAT CAG TTT GTA<br>Phe Tyr Asp Ala Ser Tyr Gly Ser Leu His Glu Thr Cys Thr Asp Gln Phe Val<br>                    40                                   50 | 216 |
| TCT CTG AGA ACC TCT GAA ACG TCA AAG ATG TCC AAC TTC ACC TTC AAG GAG AGC<br>Ser Leu Arg Thr Ser Glu Thr Ser Lys MET Ser Asn Phe Thr Phe Lys Glu Ser<br>                          60                              70 | 270 |
| CGG GTG ACA GTA TCA GCA ACG TCA AGC AAC GGG AAG ATT CTG AAG AAG AGA CGG<br>Arg Val Thr Val Ser Ala Thr Ser Ser Asn Gly Lys Ile Leu Lys Lys Arg Arg<br>                                  80 | 324 |
| CTG AGT TTC AGT GAG ACC TTC ACT GAA GAT GAC CTG CAG TCC ATA ACC CAT GAT<br>Leu Ser Phe Ser Glu Thr Phe Thr Glu Asp Asp Leu Gln Ser Ile Thr His Asp<br>        90                                  100 | 378 |
| CTG GAA GAG ACC ATC CAA CCC AGA TCA GCA CCT TAC ACC TAC CAG AGT GAT TTG<br>Leu Glu Glu Thr Ile Gln Pro Arg Ser Ala Pro Tyr Thr Tyr Gln Ser Asp Leu<br>                110                              120 | 432 |
| AGA TAC AAA CTG ATG AAG CTC GTC AGG CAG AAG TTT GTC ATG AAT GAT TCC CTC<br>Arg Tyr Lys Leu MET Lys Leu Val Arg Gln Lys Phe Val MET Asn Asp Ser Leu<br>                    130                          140 | 486 |
| AAC CAA ACT ATA TAT CAG GAT GTG GAC AAA CAC TAT CTC AGC ACC ACT TGG TTA<br>Asn Gln Thr Ile Tyr Gln Asp Val Asp Lys His Tyr Leu Ser Thr Thr Trp Leu<br>                          150                        160 | 540 |
| AAT GAC CTG CAA CAG GAA GTA AAA TTT GAC ATG TAT GCC TAC TCG TCG GGA GGA<br>Asn Asp Leu Gln Gln Glu Val Lys Phe Asp MET Tyr Ala Tyr Ser Ser Gly Gly<br>                                  170 | 594 |
| GAC GAC TCT AAA TAT CCT GTT ACT CTA AAA ATC TCA GAT TCA CAA CTG TTC GTG<br>Asp Asp Ser Lys Tyr Pro Val Thr Leu Lys Ile Ser Asp Ser Gln Leu Phe Val<br>    180                                    190 | 648 |

FIG. 1B

| | |
|---|---|
| AGC GCT CAA GGA GAA GAC CAG CCC GTG TTG CTG AAG GAG TTG CCA GAA ACA CCA<br>Ser Ala Gln Gly Glu Asp Gln Pro Val Leu Leu Lys Glu Leu Pro Glu Thr Pro<br>           200                                         210 | 702 |
| AAA CTC ATC ACA GGT AGT GAG ACC GAC CTC ATT TTC TTC TGG AAA AGT ATC AAC<br>Lys Leu Ile Thr Gly Ser Glu Thr Asp Leu Ile Phe Phe Trp Lys Ser Ile Asn<br>                  220                                         230 | 756 |
| TCT AAG AAC TAC TTC ACA TCA GCT GCT TAT CCA GAG CTG TTT ATT GCC ACC AAA<br>Ser Lys Asn Tyr Phe Thr Ser Ala Ala Tyr Pro Glu Leu Phe Ile Ala Thr Lys<br>                              240                                 250 | 810 |
| GAA CAA AGT CGG GTG CAC CTG GCA CGG GGA CTG CCC TCT ATG ACA GAC TTC CAG<br>Glu Gln Ser Arg Val His Leu Ala Arg Gly Leu Pro Ser MET Thr Asp Phe Gln<br>                                      260 | 864 |
| ATA TCA TAA AAG CAG CCT TAT TTC GGG AGT CTA TTC ACT TGG AAG TGC TGA ACA<br>Ile Ser<br>   270 | 918 |
| GTC TGT ATG TAC CAT GTA CAG GAA CCT TCC TCA CCC TGA GTC ACT TGC ACA GCA | 972 |
| TGT GCT GAG TCT CTG TAA TTC TAA ATG AAT GTT TAC CCT CTT TGT AAG AGA AGA | 1026 |
| GCA AAC CCT AGT GGA GCC ACC CCG ACA TAT GAT ACT ATC TGT TAT TTT AAA GAG | 1080 |
| TAC CCT ATA GTT TGC TCA GTA CTA ATC ATT TTA ATT ACT ATT CTG CAT GGC ATT | 1134 |
| CTT AGG AGG ATC AAA AAG ACT CTA CAC ATA TTA CAG ATG GGT TAA CAA AGG GAT | 1188 |
| AAA ACA ACT GAA AAG CAC ACT CAA TGC ATT TGG AAT ATA AAT TCA CAG ACC AAT | 1242 |
| CTC ACT GTG CAC CTT CGG CTT CAA AAT GCC AGT TGA GTA GGA TAA AGG TAT AAG | 1296 |
| AAC TTA ATG CTG TCA TTT TCA AAA GGA AGG GGA CAA TAG CTA CAT CTT TCC TAC | 1350 |
| CTC AGT GGG TTT TAC TCC AGT GAG ATC ATT TGG ATG AAA TCC TCC TGT AAC AGA | 1404 |
| CCT CAA GAA GGA GAC AGA CTG TTG AAT GTT ATT TTT AAG TTA TTT TAT ATA TGT | 1458 |
| ATT TAT AAA TAT ATT TAT GAT AAT TAT ATT ATT TAT GGA ACA TCC TTA AAT CCT | 1512 |
| CTG AGC TTG ACA GGC ATC CTC ACA GCA GGA TTT TCT AGG TGG TCA GTT AGA TAT | 1566 |
| AGT TTC CTC TAG AGC ACC ATG CTA CAG ACT TTA CAC TTT TTC CAC AGC CAC GAA | 1620 |
| GCT CTC TGT ACA TTC CTG TAC TTG GGA GCC CTT TCA TCA TGA TCT TAA TCT GTA | 1674 |
| CTG TTT ACT TTG TTC ATC TAA AAT GAT AAT TGA GTC AGT CTT TTT CCC TCC CAT | 1728 |
| CCT TAA AGC TGT CTG GGT ATT CTT ACA TCA TTC AGT CTC ACC TGT AAC TAA CAC | 1782 |
| CAA CCA TCT AAA GAT GGA AAG AGC TTA ACT GTG ACA ACC ACA TCA CTG TTA CCT | 1836 |
| GAA GTT TCT TTT CTA GAA TGT AAT CAG TGT TTC CCC TGG ATT CCA ATT TTT TTT | 1890 |
| TCA AAC CAC AGT ATC ATG TAA CTA TCA ACA ATA ACA ATC AAC TCA TTA TTA TTA | 1944 |
| ATC ATA ATT AAA TAA AAC AAG TTT GAG CTG AAA AAA AAA AA | 1974 |

FIG. 2A

```
                          27                                              54
ATC AAG CCT AGG TCA GCA CCT TTT AGC TTC CTG AGC AAT GTG AAA TAC AAC TTT
Ile Lys Pro Arg Ser Ala Pro Phe Ser Phe Leu Ser Asn Val Lys Tyr Asn Phe 81                                             108
ATG AGG ATC ATC AAA TAC GAA TTC ATC CTG AAT GAC GCC CTC AAT CAA AGT ATA
MET Arg Ile Ile Lys Tyr Glu Phe Ile Leu Asn Asp Ala Leu Asn Gln Ser Ile 135                                             162
ATT CGA GCC AAT GAT CAG TAC CTC ACG GCT GCT GCA TTA CAT AAT CTG GAT GAA
Ile Arg Ala Asn Asp Gln Tyr Leu Thr Ala Ala Ala Leu His Asn Leu Asp Glu 189                                             216
GCA GTG AAA TTT GAC ATG GGT GCT TAT AAG TCA TCA AAG GAT GAT GCT AAA ATT
Ala Val Lys Phe Asp MET Gly Ala Tyr Lys Ser Ser Lys Asp Asp Ala Lys Ile 243                                             270
ACC GTG ATT CTA AGA ATC TCA AAA ACT CAA TTG TAT GTG ACT GCC CAA GAT GAA
Thr Val Ile Leu Arg Ile Ser Lys Thr Gln Leu Tyr Val Thr Ala Gln Asp Glu 297                                             324
GAC CAA CCA GTG CTG CTG AAG GAG ATG CCT GAG ATA CCC AAA ACC ATC ACA GGT
Asp Gln Pro Val Leu Leu Lys Glu MET Pro Glu Ile Pro Lys Thr Ile Thr Gly 351                                             378
AGT GAG ACC AAC CTC CTC TTC TTC TGG GAA ACT CAC GGC ACT AAG AAC TAT TTC
Ser Glu Thr Asn Leu Leu Phe Phe Trp Glu Thr His Gly Thr Lys Asn Tyr Phe 405                                             432
ACA TCA GTT GCC CAT CCA AAC TTG TTT ATT GCC ACA AAG CAA GAC TAC TGG GTG
Thr Ser Val Ala His Pro Asn Leu Phe Ile Ala Thr Lys Gln Asp Tyr Trp Val 459                                             486
TGC TTG GCA GGG GGG CCA CCC TCT ATC ACT GAC TTT CAG ATA CTG GAA AAC CAG
Cys Leu Ala Gly Gly Pro Pro Ser Ile Thr Asp Phe Gln Ile Leu Glu Asn Gln

513
GCG
Ala
```

FIG. 2B-1

```
CAT TTC ATT GGC GTT TGA GTC AGC AAA GAA GTC AAG ATG GCC AAA GTT CCA GAC        54
                                                MET Ala Lys Val Pro Asp

ATG TTT GAA GAC CTG AAG AAC TGT TAC AGT GAA AAT GAA GAA GAC AGT TCC TCC       108
MET Phe Glu Asp Leu Lys Asn Cys Tyr Ser Glu Asn Glu Glu Asp Ser Ser Ser
             10                                      20

ATT GAT CAT CTG TCT CTG AAT CAG AAA TCC TTC TAT CAT GTA AGC TAT GGC CCA       162
Ile Asp His Leu Ser Leu Asn Gln Lys Ser Phe Tyr His Val Ser Tyr Gly Pro
                         30                                      40

CTC CAT GAA GGC TGC ATG GAT CAA TCT GTG TCT CTG AGT ATC TCT GAA ACC TCT       216
Leu His Glu Gly Cys MET Asp Gln Ser Val Ser Leu Ser Ile Ser Glu Thr Ser
                             50                                      60

AAA ACA TCC AAG CTT ACC TTC AAG GAG AGC ATG GTG GTA GTA GCA ACC AAC GGG       270
Lys Thr Ser Lys Leu Thr Phe Lys Glu Ser MET Val Val Val Ala Thr Asn Gly
                                     70

AAG GTT CTG AAG AAG AGA CGG TTG AGT TTA AGC CAA TCC ATC ACT GAT GAT GAC       324
Lys Val Leu Lys Lys Arg Arg Leu Ser Leu Ser Gln Ser Ile Thr Asp Asp Asp
         80                                      90

CTG GAG GCC ATC GCC AAT GAC TCA GAG GAA GAA ATC ATC AAG CCT AGG TCA GCA       378
Leu Glu Ala Ile Ala Asn Asp Ser Glu Glu Glu Ile Ile Lys Pro Arg Ser Ala
                     100                                     110

CCT TTT AGC TTC CTG AGC AAT GTG AAA TAC AAC TTT ATG AGG ATC ATC AAA TAC       432
Pro Phe Ser Phe Leu Ser Asn Val Lys Tyr Asn Phe MET Arg Ile Ile Lys Tyr
                         120                                     130

GAA TTC ATC CTG AAT GAC GCC CTC AAT CAA AGT ATA ATT CGA GCC AAT GAT CAG       486
Glu Phe Ile Leu Asn Asp Ala Leu Asn Gln Ser Ile Ile Arg Ala Asn Asp Gln
                             140                                     150

TAC CTC ACG GCT GCT GCA TTA CAT AAT CTG GAT GAA GCA GTG AAA TTT GAC ATG       540
Tyr Leu Thr Ala Ala Ala Leu His Asn Leu Asp Glu Ala Val Lys Phe Asp MET
                                 160

GGT GCT TAT AAG TCA TCA AAG GAT GAT GCT AAA ATT ACC GTG ATT CTA AGA ATC       594
Gly Ala Tyr Lys Ser Ser Lys Asp Asp Ala Lys Ile Thr Val Ile Leu Arg Ile
         170                                     180

TCA AAA ACT CAA TTG TAT GTG ACT GCC CAA GAT GAA GAC CAA CCA GTG CTG CTG       648
Ser Lys Thr Gln Leu Tyr Val Thr Ala Gln Asp Glu Asp Gln Pro Val Leu Leu
             190                                     200
```

FIG. 2B-2

| | |
|---|---|
| AAG GAG ATG CCT GAG ATA CCC AAA ACC ATC ACA GGT AGT GAG ACC AAC CTC CTC | 702 |
| Lys Glu MET Pro Glu Ile Pro Lys Thr Ile Thr Gly Ser Glu Thr Asn Leu Leu | |
|               210                          220 | |
| TTC TTC TGG GAA ACT CAC GGC ACT AAG AAC TAT TTC ACA TCA GTT GCC CAT CCA | 756 |
| Phe Phe Trp Glu Thr His Gly Thr Lys Asn Tyr Phe Thr Ser Val Ala His Pro | |
|              230                        240 | |
| AAC TTG TTT ATT GCC ACA AAG CAA GAC TAC TGG GTG TGC TTG GCA GGG GGG CCA | 810 |
| Asn Leu Phe Ile Ala Thr Lys Gln Asp Tyr Trp Val Cys Leu Ala Gly Gly Pro | |
|                  250 | |
| CCC TCT ATC ACT GAC TTT CAG ATA CTG GAA AAC CAG GCG TAG GTC TGG AGT CTC | 864 |
| Pro Ser Ile Thr Asp Phe Gln Ile Leu Glu Asn Gln Ala  . | |
| 260                            270 | |
| ACT TGT CTC ACT TGT GCA GTG TTG ACA GTT CAT ATG TAC CAT GTA CAT GAA GAA | 918 |
| GCT AAA TCC TTT ACT GTT AGT CAT TTG CTG AGC ATG TAC TGA CCC TTG TAA TTC | 972 |
| TAA ATG AAT GTT TAC ACT CTT TGT AAG AGT GGA ACC AAC ACT AAC ATA TAA TGT | 1026 |
| TGT TAT TTA AAG AAC ACC CTA TAT TTT GCA TAG TAC CAA TCA TTT TAA TTA TTA | 1080 |
| TTC TTC ATA ACA ATT TTA GGA GGA CCA GAG CTA CTG ACT ATG GCT ACC AAA AAG | 1134 |
| ACT CTA CCC ATA TTA CAG ATG GGC AAA TTA AGG CAT AAG AAA ACT AAG AAA TAT | 1188 |
| GCA CAA TAG CAG TTG AAA CAA GAA GCC ACA GAC CTA GGA TTT CAT GAT TTC ATT | 1242 |
| TCA ACT GTT TGC CTT CTA CTT TTA AGT TGC TGA TGA ACT CTT AAT CAA ATA GCA | 1296 |
| TAA GTT TCT GGG ACC TCA GTT TTA TCA TTT TCA AAA TGG AGG GAA TAA TAC CTA | 1350 |
| AGC TTC CTG CCG CA ACA GTT TTT TAT GCT AAT CAG GGA GGT CAT TTT GGT AAA | 1404 |
| ATA CTT CTT GAA GCC GAG CCT CAA GAT GAA GGC AAA GCA CGA AAT GTT ATT TTT | 1458 |
| TAA TTA TTA TTT ATA TAT GTA TTT ATA AAT ATA TTT AAG ATA ATT ATA ATA TAC | 1512 |
| TAT ATT TAT GGG AAC CCC TTC ATC CTC TGA GTG TGA CCA GGC ATC CTC CAC AAT | 1566 |
| AGC AGA CAG TGT TTT CTG GGA TAA GTA AGT TTG ATT TCA TTA ATA CAG GGC ATT | 1620 |
| TTG GTC CAA GTT GTG CTT ATC CCA TAG CCA GGA AAC TCT GCA TTC TAG TAC TTG | 1674 |
| GGA GAC CTG TAA TCA TAT AAT AAA TGT ACA TTA ATT ACC TTG AGC CAG TAA TTG | 1728 |
| GTC CGA TCT TTG ACT CTT TTG CCA TTA AAC TTA CCT GGG CAT TCT TGT TTC ATT | 1782 |
| CAA TTC CAC CTG CAA TCA AGT CCT ACA AGC TAA AAT TAG ATG AAC TCA ACT TTG | 1836 |
| ACA ACC ATG AGA CCA CTG TTA TCA AAG TTG AGT TCA TCT AAT TTT AGC TTG TAG | 1890 |
| AGA CGG GAT TTC ACC ATC TTG GCC GTG CTG GTC TCG AAC TTC TGA CCT CGT GAT | 1944 |
| CCA CCC GCC TCG GCC TCC CAA AGT GCT GGG ATT ACA GGC GTG AGC CAT CGC GCC | 1998 |
| CGG CCT GGA GTT TCT ACT GTG CAC CAG GCA CTA CCT TTA CAT GTA TTG TTT TAT | 2052 |
| TTA ATC CTC AGT CAG CCG TGT TTG GTA GGT GCA GTT AGT ATA TTT CCA TTT TCA | 2106 |
| TCT GCG CAA ACA GAT TCA GGA ACT TTG TAA TTT ACA TAA GGT CAC ATT CAT CCT | 2160 |
| AAT TCA CAA AAT CAA GAT TTC ACA CCT ATT CCT TTT TCT TTC CAG TGC CTG TGC | 2214 |
| TTT TTC TCT CAT ACC AAG GAG AAG TAA TAA GCC TAA CGT TTT AAA CCT CAC AAA | 2268 |
| AGT ACA TAC AGA AAA GTA AAT AGC CTA ATT TTG CAA CTA ATA CAA ATG GCG CTG | 2322 |
| TAC TTC TTT GGT GAT GGT AGA TTT ATA ATT TTT GAA GTA TGG TAG ATT CAA ATG | 2376 |
| AAC CAC TGA AAA GGC ATT TAG TTT CTT GTC CCA AAT AAA AAA AAA AAA AAA AAA | 2430 |

FIG. 3

```
      X         10         20         30         40         50         60
      MAKVPDLFEDLKNCYSENEDYSSAIDHLSLNQKSFYDASYGSLHETCTDQFVSLRTSETS       mouse
      ::::::  :::::::::::::   ::::::::::::   :::  :::  :  ::  :::    ::::
      MAKVPDMFEDLKNCYSENEEDSSSIDHLSLNQKSFYHVSYGPLHEGCMDQSVSLSISETS       human
      X         10         20         30         40         50         60

70         80         90        100        110
      KMSNFTFKESRVTVSATSSNGKILKKRRLSFSETFTEDDLQSITHDLEETIQ-PRSAPYT       mouse
      :  :    ::::::  : :        :::  :::::::: :       :::  :  ::  :   :::::
      KTSKLTFKESMVVVAT---NGKVLKKRRLSLSQSITDDDLEAIANDSEEEIIKPRSAPFS       human
                70         80         90        100        110

130        140        150        160        170
      YQSDLRYKLMKLVRQKFVMNDSLNQTIYQDVDKHYLSTTWLNDLQQEVKFDMYAYSSGGD       mouse
         :    :   :         :   ::  :::  :        :   ::         :   :    :::::  ::   :
      FLSNVKYNFMRIIKYEFILNDALNQSIIRANDQ-YLTAAALHNLDEAVKFDMGAYKSSKD       human
          120        130        140        150        160        170

190        200        210        220        230
      DSKYPVTLKISDSQLFVSAQGEDQPVLLKELPETPKLITGSETDLIFFWKSINSKNYFTS       mouse
         :    :    :  :::   :::      :   :::::::::: ::   ::   ::::::   :   :::      ::::::
      DAKITVILRISKTQLYVTAQDEDQPVLLKEMPEIPKTITGSETNLLFFWETHGTKNYFTS       human
          180        190        200        210        220        230

250        260        x
      AAYPELFIATKEQSRVHLARGLPSMTDFQIS                                    mouse
         :   :   ::::::::      :   ::  :  ::    :::::
      VAHPNLFIATKQDYWVCLAGGPPSITDFQILENQA                               human
              240        250        260        270X
```

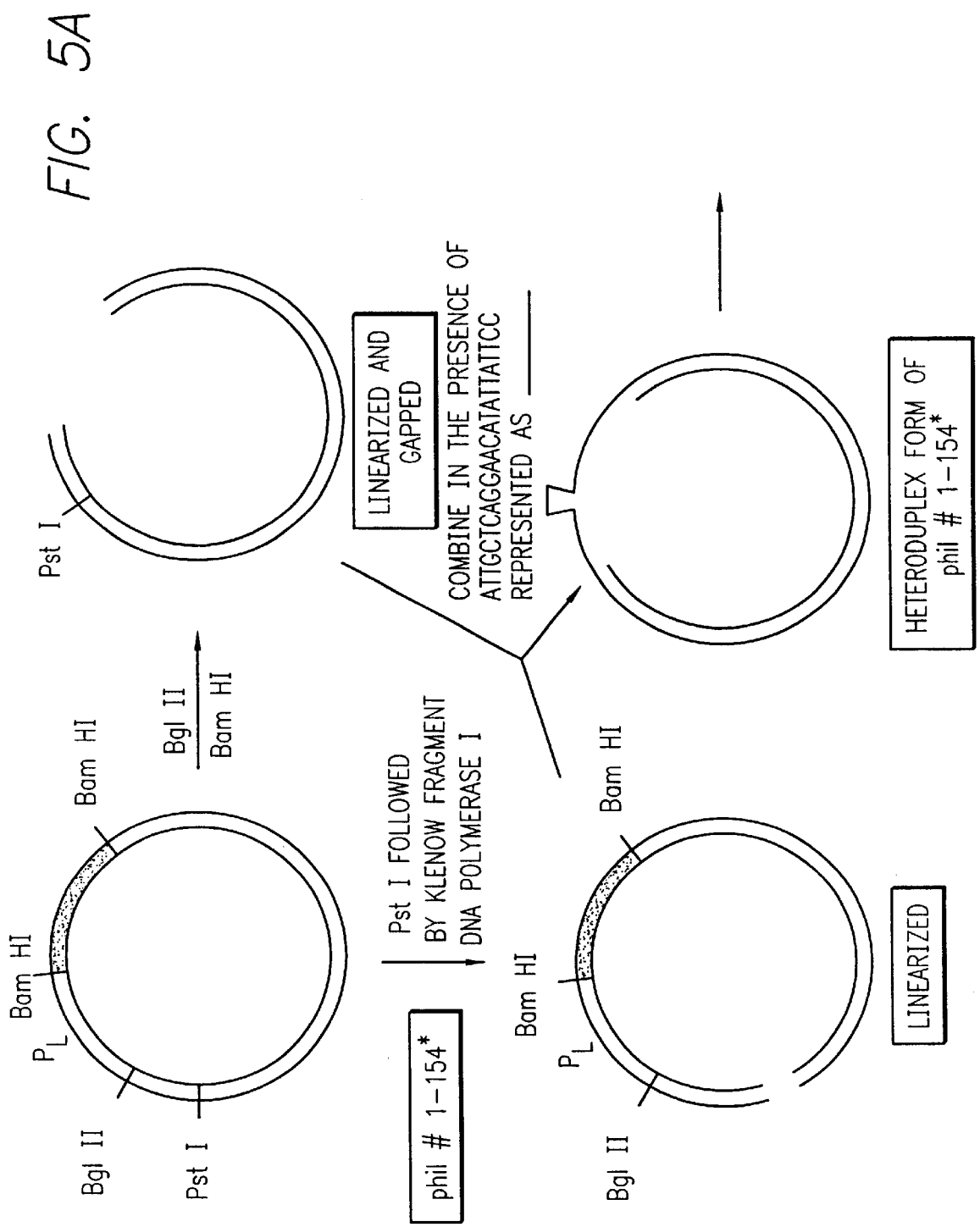

RECOMBINANT HUMAN RECOMBINANT HUMAN INTERLEUKIN-1α

This application is a divisional of application Ser. No. 08/259,927, filed Jun. 15, 1994, U.S. Pat. No. 5,936,066, which is a continuation of application Ser. No. 07/028,429, filed Mar. 20, 1987, abandoned, which is a continuation of application Ser. No. 06/748,632, filed Jun. 24, 1985, abandoned, which is a continuation-in-part of application Ser. No. 06/720,774, filed Apr. 25, 1985, abandoned.

BACKGROUND OF THE INVENTION

Interleukin-1 (IL-1) is a protein synthesized and secreted by activated macrophages. As part of the body's defense mechanism against infection and other forms of injury, this polypeptide hormone stimulates the proliferation and/or differentiation of a broad spectrum of cell types (including T and B lymphocytes, liver cells, bone marrow cells, connective tissue elements, skeletal muscle, brain cells, etc.). Through its actions on these diverse cell populations, IL-1 modulates immune function, fever, liver cell function (increased synthesis and secretion of acute phase reactants: increased uptake of amino acids, iron and zinc), production and release of neutrophils from the bone marrow, skeletal muscle proteolysis, changes in connective tissue, etc. IL-1 has also been described in the prior art as lymphocyte activating factor (LAF), leukocyte endogeneous mediator (LEM), endogeneous pyrogen (EP), and mononuclear cell factor (MCF). Until recently all studies of IL-1 were conducted with partially purified protein preparations, therefore, it has not been certain whether all the activities associated with IL-1 are contained within one molecule, or whether fragments of IL-1 or other macrophage proteins are responsible for certain of the functions outlined above.

Since it has been difficult to prepare sufficient amounts of human IL-1 for structural and activity studies, the biochemical nature of this molecule is poorly understood. IL-1 preparations show evidence of size and charge heterogeneity. IL-1 activity is associated with single polypeptide chains with molecular weights anywhere in the range between 12,000 and 19,000.

Recently, the gene coding for mouse IL-1 was cloned, sequenced, and expressed in *Escherichia Coli*. See in this regard Lomedico et al., Nature 312, pp. 458–462 (Nov. 29, 1984). In conjunction with the sequencing studies on purified "natural" mouse IL-1, it is possible to understand how this hormone is synthesized to yield the population of molecules possessing size and charge heterogeneity. When purified natural mouse IL-1 is electrophoresed on SDS-polyacrylamide gels, one finds multiple polypeptides with molecular weights between 12,000 and 19,000, all of which are biologically active. These polypeptides have different amino-terminal sequences and demonstrate charge heterogeneity on Tris-glycinate polyacrylamide gels. Sequencing of the cloned mouse IL-1 cDNA and in vitro translation experiments proved that IL-1 is initially synthesized as a precursor polypeptide of 270 amino acids. Biologically active IL-1 can be obtained from *E. coli* by expressing the carboxy-terminal 156 amino acids of this precursor. Hence, IL-1 activity is proteolytically released from the carboxy-terminus of the 270 amino acid precursor protein. Multiple points of protease attack will generate a population of molecules with "ragged" amino-termini, thus providing an explanation of the size and charge heterogeneity observed in purified "natural" IL-1.

The cloning of a putative gene for human IL-1 was described by Auron et al., Proc. Natl. Acad. Sci. USA, 81, 7907 (1984) which was published in February 1985. The DNA and protein sequences described therein are only partially homologous to the sequences described below.

The purification of natural human IL-1 to homogeneity has been reported by Lachman, Fed. Proc. 42, No. 3. 2639–2645 (June 1983). The method used molecular weight fractionation, isoelectric focusing and preparative polyacrylamide gel electrophoresis. Due to the use of sodium dodecyl sulfate in the last step, the product was denatured and exhibited only a trace of its original biological activity. See also Schmidt, J. Exp. Med. 160, 772–787 (September 1984) for a purification scheme using HPLC methods to produce a single charged species of human IL-1 and Kronheim et al., J. Exp. Med. 161, 490–502 (March 1985).

It has also been known in the art to produce antibodies directed against murine IL-1. See Mizel et al. J. Immun. 131, 1834 (1983). These antibodies, which were raised in goat, were utilized to develop an assay for IL-1 and also in the production of an anti-IL-1 immunoabsorbent column which in turn is useful for further purification of either natural or recombinant murine IL-1. The anti murine IL-1 antibody crossreacts poorly with human IL-1.

SUMMARY OF THE INVENTION

The present invention relates to the cloning of the human IL-1 gene, its engineering into suitable expression vectors, transformation of host organisms with such expression vectors and production of biologically active recombinant human IL-1 by culture of such transformed cells. Additionally, the present invention relates to the isolation and use of the resulting recombinant human IL-1 polypeptide.

Thus, the present invention utilizes recombinant DNA technology as the means to discover the DNA sequence and the deduced amino acid sequence for human interleukin-1 and to its production and to its use.

More particularly, the present invention relates to the isolation and identification of DNA sequences coding for biologically active forms of human interleukin-1. This was accomplished by employing a mouse IL-1 cDNA clone to isolate a partial human IL-1 genomic clone. This genomic clone was used in turn to isolate a human IL-1 cDNA clone. The sequence of this cDNA revealed the structure of the human IL-1 precursor protein. Expression of the carboxy-terminal 154 amino acids of this precursor in *E. coli* resulted in the production of biologically active IL-1 protein.

Thus, more particularly, the present invention relates to the isolation and identification of DNA sequences encoding the human IL-1 precursor and biologically active molecules contained therein, and to the construction of recombinant DNA expression vehicles containing such DNA sequences operatively linked to expression—effecting promoter sequences and to the expression vehicles so constructed. In another aspect, the present invention relates to host culture systems, such as various microorganism and vertebrate cell cultures transformed with such expression vehicles and thus directed in the expression of the DNA sequences referred to above. In other aspects, this invention relates to the means and methods of converting the end products of such expression to novel entities, such as pharmaceutical compositions, useful for the prophylactic or therapeutic treatment of humans or in diagnostic assay systems. In preferred embodiments, this invention provides particular expression vehicles that are constructed properly such that human interleukin-1 is produced in the host cell in mature form.

BRIEF DESCRIPTION OF THE DRAWINGS

The present invention will be more readily understood when considered in connection with the accompanying drawings wherein:

FIGS. 1A and 1B shows the nucleotide sequence and predicted amino acid sequence of mouse IL-1 precursor cDNA.

FIG. 2A shows the nucleotide sequence and predicted amino acid sequence of the carboxy-terminal region of human IL-1 precursor (from phil #7) with the partial sequence of phil #4 indicated by underlining, while 2B-1 and 2B-2 shows the nucleotide sequence and predicted amino acid sequence of the human IL-1 precursor as deduced from a composite of clones phil #7 and phil #19.

FIG. 3 illustrates the sequence homology of the mouse and human IL-1 precursor proteins.

FIGS. 5A and 5B is a flow chart showing the construction of expression vector (phil #1-154) which directs the synthesis of the 154 amino acid carboxy terminal sequence of human IL-1 without the extraneous amino acids at the amino terminus of phil #1-154*.

BRIEF DESCRIPTION OF THE PREFERRED EMBODIMENT

Figure 4:
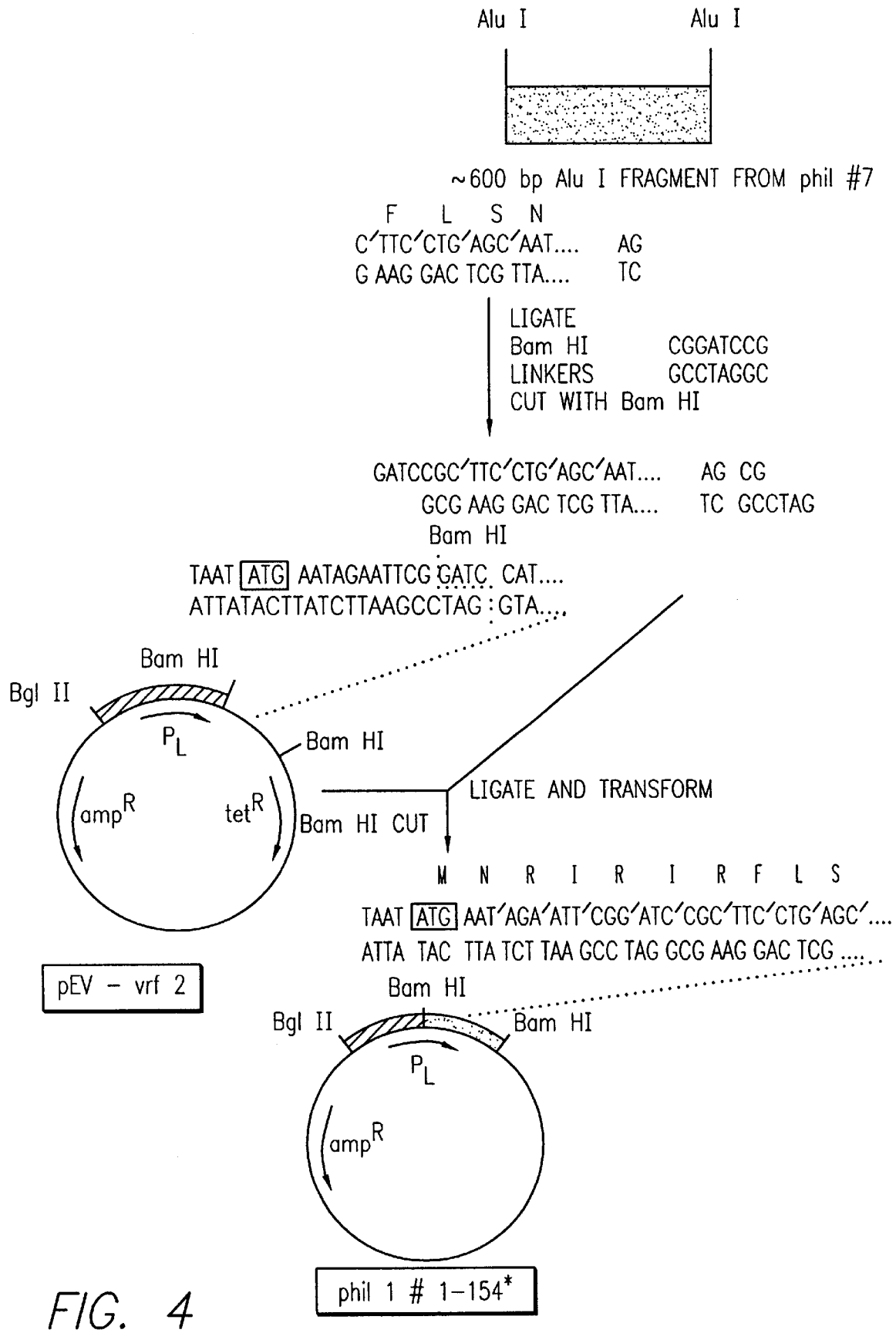
FIG. 4 is a flow chart showing the construction of an expression vector which directs the synthesis of a modified 154 amino acid carboxy terminal sequence of human IL-1 (phil #1-154*) using pEV-vrf 2 as a vector.

As indicated above the cloned gene coding for a human IL-1 polypeptide may be obtained by use of a mouse IL-1 cDNA clone as a hybridization probe. In such a procedure, an EcoRl partial human genomic phage library (Fritsch et al. cell 19, 959–972 (1980)) was screened using as the hybridization probe the plasmid pIL-1 1301 (Lomedico et al. supra). Phage plaques were transferred to nitrocellulose filters by standard methods (Maniatis et al. Molecular Cloning A Laboratory Manual, Cold Spring Harbor Laboratory, Cold Spring Harbor, N.Y., 1982) and the filters containing the imobilized DNA were hybridized ($10^6$ cpm/10 ml/138 mm filter) in 5×SSPE (1×SSPE=0.18M NaCl, 10 mM Na phosphate pH 7.0, 1 mM $Na_3$ EDTA). 5×Denhardt's (0.1% Ficoll 400, 0.1% bovine serum albumin, 0.1% polyvinylpyrrolidine (w/v)), 0.3% SDS, 20% formamide, 250 microgram/ml of calf thymus DNA, and $^{32}$P—pIL-1 1301 (labelled by nick translation to $1-2\times10^8$ cpm/microgram) for 48 hours at 37° C. The filters were washed at 30° C. in 0.5×SSPE and autoradiographed. After screening $7.9\times10^5$ plaques, 2 positive recombinant phage were identified. These two phage were shown to be identical by restriction endonuclease mapping and named λ-hil 4. Using the hybridization conditions described above, the mouse IL-1 cDNA clone pIL-1 1301 was subsequently shown to specifically hybridize to a 1.4 kb EcoRl-Hind III fragment from the recombinant phage λ-hil 4. This 1.4 kb fragment was subcloned into pBR322 to yield phil #4. The nucleotide sequence proximal to the EcoRl site of phil #4 was determined (see FIG. 2A) and compared to the sequence of mouse IL-1 mRNA and protein. This analysis showed 75% nucleic acid homology and 66% amino acid sequence homology with the carboxy-terminal 61 amino acids of the mouse IL-1 precursor and its accompanying 3' non-coding region.

The partial human IL-1 gene obtained as above was then employed as a probe to isolate a human IL-1 cDNA clone derived from mRNA obtained from induced normal human peripheral blood leukocytes. The human leukocyte concentrates, collected and prepared from normal donors were obtained from the American Red Cross, Lansing, Mich. The contents from 50–100 leukocyte concentrates were aseptically removed from the collection bags and pooled. The leukocyte pool was mixed with a half volume of a 6% solution of hetastarch (Hespan, American Hospital Supply Corp., Irvine, Calif.) in a separatory funnel and allowed to stand for 3–3.5 hours at room temperature. This procedure differentially sedimented the contaminating red blood cells from the leukocytes. The volume of the leukocyte—Hespan mixture should not exceed two-thirds of the volume of the separatory funnel to insure proper sedimentation. The red blood cells sedimented to the bottom of the separatory funnel and cell separation was complete when a sharp interface band of white cells was apparent just above the red cell layer. The "low density" white blood cells were used for the production of interleukin-1. These cells were removed from the separatory funnel by carefully aspirating only the uppermost layer of cells located above the interface white cells. The low density leukocytes were removed from the Hespan by sedimentation in 250 ml conical centrifuge tubes (Corning Glassworks, Corning, N.Y.) at 500×g for 20 minutes. The pellet was resuspended in 9 volumes of a 0.83% solution of ammonium chloride for 5 minutes to lyse the remaining red blood cells. The leukocytes were removed from the ammonium chloride solution by sedimentation at 500×g for 10 minutes as described above.

The cell pellet was then resuspended to a concentration not exceeding $3.5\times10^7$ cells/ml in RPMI—1640 medium (GIBCO) prewarmed to 37° C. No fetal calf serum was added to the medium to avoid clumping of the concentrated cells. The freshly isolated leukocytes, free of red blood cell contamination, were diluted in the induction vessel with the appropriate volume of RPMI—1640 medium supplemented with 2% fetal calf serum to make a final concentration of $3\times10^6$ cells/ml. The cells were incubated at 37° C. for one hour and induced for production of IL-1 by the addition of 10 g/ml E. coli lipopolysaccharide B (LPS, Difco 3880-25). Incubation was continued for 12 hours for mRNA extraction. The cells were then removed from the induction medium by sedimentation at 500×g. Cells induced for mRNA extraction may be stored as a frozen pellet at minus 20° C. or lower.

A particularly preferred procedure for isolating poly(A)$^+$ RNA from human peripheral blood leukocytes induced with LPS is the guanidine thiocyanate-CsCl method of Chirgwin et al. (Biochemistry 18, 5294–5299, 1979) and oligo (dT)-cellulose chromatography (Aviv and Leder, Proc. Natl. Acad. Sci. 69, 1408–1412, 1972). Northern blot analysis of this RNA demonstrated that clone phil #4 specifically hybridized to a mRNA approximately 2,100 nucleotides long. Total poly (A)$^+$ RNA was fractionated by sucrose density gradient centrifugation and mRNA with sizes between 1,000 and 3,000 nucleotides was collected. Using this enriched mRNA pool, a cDNA library of approximately 20,000 clones was constructed in pBR 322 by established procedures (see Gubler and Hoffman, Gene 25, 263–269, 1983). This library was screened using as a hybridization probe the 1.4 kb EcoRl-Hind III insert from plasmid phil #4. Bacterial colonies were transferred to nitrocellulose filters by standard methods (Maniatis et al. supra) and the filters containing the immobilized DNA were hybridized in 5×SSPE, 5×Denhardts, 0.3% SDS, 50% formamide (w/v), 250 micro g/ml calf thymus DNA and $^{32}$P-phil #4 insert DNA for 16 hours at 37° C. The filters were washed at 50° C. in 0.1×SSPE and autoradiographed to identify a single positive clone termed phil #7. This clone contains an insert of 2,200 bp. The nucleotide sequence of this insert (see FIG. 2A) contains the partial sequence of the genomic clone phil #4 and hence corresponds to the cDNA sequence of mRNA encoded by this gene. The nucleotide sequence of this phil

7 insert predicts an open reading frame for a protein of 163 amino acids. This predicted protein is 55% homologous (see FIG. 3) to the carboxy-terminal 160 amino acids of the mouse IL-1 precursor. Hence the sequence provided by phil #7 represents the carboxy-terminal region of the human IL-1 precursor. Primer extension experiments demonstrate that approximately 400 nucleotides from the 5' end of the human IL-1 mRNA are missing from clone phil #7.

Since human IL-1 cDNA clone #7 turned out to be an incomplete copy of human IL-1 mRNA, the following strategy to complete the sequence was adapted: Based on the DNA sequence of clone #7, a synthetic oligonucleotide with the sequence 5'-GGGCGTCATTCAGGATGAATTCGTA-3' was devised and synthesized using solid support phosphoramidite technology. This oligonucleotide is complementary to the sequence coding for amino acids 20–28 as predicted from phil #7. The oligonucleotide spans a region in the cDNA predicted to contain an EcoRI restriction site. Such a site is useful for fusing an extension clone with clone #7 to create a cDNA encompassing the complete protein coding region for the human IL-1 precursor. This oligonucleotide was annealed to size-fractionated poly $A^+$ RNA from LPS—induced human peripheral blood leukocytes (supra). Annealing conditions were 50 mM NaCl, 10 mM DTT, 0.05 mM EDTA. 550 pmoles oligonucleotide/ml, 250 mcg of poly $A^+$RNA/ml for one minute at 90° C., 10' at 43° C., 10' at 20° C. after which the reaction was cooled on ice. cDNA—synthesis and establishment of an extension cDNA—library were performed as described above for clone #7. About $10^5$ independent transformants were generated in this way from 5 mcg of poly $A^+$ RNA enriched for human IL-1 mRNA. A total of approximately 2900 were screened with the oligonucleotide described above that had been labelled with polynucleotide kinase and $\gamma$-$^{32}$P-ATP according to standard procedures (Maniatis et al., supra). Colony bearing nitrocellulose filters were made according to standard procedures (Maniatis et al., supra). The filters were hybridized with the labelled oligonucleotide under the following conditions: 5×SSPE, 10×Denhardts, 0.1% SDS, 100 µg/ml yeast soluble RNA; 0.2 pmoles/ml of labelled oligonucleotide (specific activity=~1 µCi/pmole) for 15' at 65° C. and subsequently 2 hours at 37° C. The filters were then washed twice in 2×SSPE—0.025% SDS (quick rinses at room temperature) and then in 4×SSPE—0.025% SDS at 51° C. for 60'. The filters were then air dried, exposed to x-ray film with the aid of an intensifying screen at −70° C. for 16 hours. Twelve positive colonies were further analyzed by restriction endonuclease cleavage. Clone phil #19 was chosen for further analysis. The sequence of the insert (see FIG. 2B) from phil #19 contains the expected overlap with phil #7 and predicts a single open reading frame coding for 139 amino acids. This region represents the amino-terminal end of the human IL-1 precursor protein, and is highly homologous to the corresponding region of the mouse IL-1 precursor protein (FIG. 3). Hence, combining the sequence information from phil #7 and phil #19, human IL-1 mRNA codes for a protein of 271 amino acids which is significantly related to the 270 amino acid mouse protein (FIG. 3).

Plasmid phil #7 contains the coding information for the carboxy-terminal 163 amino acids of the 271 amino-acid human IL-1 precursor protein. Plasmid phil #19 contains the coding information for the amino-terminal 139 amino acids of this protein. Each plasmid possesses a single EcoRI restriction endonuclease cleavage site within the sequence (94 nucleotides long) that is common to their inserts. This EcoRI site can be used to join the information from the two plasmids into a single composite plasmid containing the entire coding region from the human IL-1 precursor protein. Using standard methods, plasmids phil #7 and phil #19 can be individually digested with EcoRI and Bam HI, and the resultant DNA fragments separated by polyacrylamide gel electrophoresis. The ~2100 bp EcoRI-Bam HI fragment can be isolated from the phil #7 digest, and the ~460 bp Bam HI—EcoRI fragment can be isolated from the phil #19 digest. The two isolated fragments can be ligated together using T4 DNA ligase. The ligase is heat-inactivated and the mixture is treated with Bam HI. This mixture can be ligated to Bam HI-linearized pEV-vrf2 (below) and used to transform E. coli strain MC1061 containing the compatible plasmid pRK248 (cIts) using selection for ampicillin resistance. Bacterial clones can be screened by restriction endonuclease cleavage analysis to identify a plasmid, phil #1-271*, which contains the expected insert in the correct orientation. Plasmid phil #1-271* is modified by site-directed oligonucleotide mutagenesis (see below) to remove the extraneous nucleotides between the initiation ATG codon and the alanine codon (GCC) which is the second amino acid in the 271 amino acid precursor protein, to generate phil #1-271. Bacteria containing phil #1-271, when induced by temperature shift (supra), synthesize the complete 271 amino acid IL-1 precursor protein as set forth in FIG. 2B.

Plasmid pEV-vrf2 is a pBR322 derivative modified using synthetic DNA oligonucleotides to contain a ribosome binding site—initiation codon downstream from a tightly regulated phage $\lambda$ $P_L$ promoter. Multiple-use restriction endonuclease cleavage sites exist immediately downstream from the initiation codon, allowing for the insertion of coding region sequences to be expressed as fusion proteins with 2–9 extra amino-terminal amino acids. These extraneous amino acids can be removed by site directed mutagenesis, resulting in the expression of the desired protein. The genealogy of pEV-vrf2 is as follows: pBR322→pRC2→pRC23→pEV-vrf2.

pRC2 is a derivative of pBR322 containing a unique BglII site adjacent (on the $amp^R$ side) to the EcoRI site in the plasmid. This plasmid was constructed using known methods in the following manner. 20 µg of pBR322 plasmid DNA was digested with EcoRI and then split into two reactions. In one, the protruding 5' single-stranded termini were removed with S1 nuclease; in the other reaction, the termini were filled-in by incorporating deoxynucleotides with the Klenow fragment of DNA polymerase I. Both reactions were terminated by phenol extraction followed by ethanol precipitation. Approximately 1 µg of DNA from each reaction was mixed with 90 pmoles of phosphorylated BglII linkers (CAGATCTG, purchased from Collaborative Research) and incubated with T4 DNA ligase at 15° for 18 hours. The ligation products were then digested with BglII and PstI and subjected to gel electrophoresis in 1% agarose. The 3600 bp and 760 bp fragments from both reactions were recovered from the gel. For the construction of pRC2, the 3600 bp from the Klenow reaction was ligated to the 760 bp fragment from the S1 reaction. E. coli strain RR1 was transformed with the ligation mixtures, and transformants were selected on LB agar plates containing 50 µg/ml ampicillin. Transformants containing the expected plasmid constructions were identified by restriction analysis of the isolated plasmid DNA. DNA sequence analysis confirmed that the S1 nuclease treatment precisely removed the 5' single-stranded termini.

pRC23 was constructed by inserting into pRC2 a 250 bp BglII-HaeIII fragment containing the $\lambda$ $P_L$ promoter joined to a pair of complementary synthetic oligonucleotides comprising a model ribosome-binding site (RBS). The HaeIII site is located within the 5' non-coding region of the λN gene 115 bp downstream of the $P_L$ transcription initiation site (Sanger, et al., 1982). Approximately 1 μg of a 450 bp BglII-HpaI fragment isolated from phage λ DNA was digested with HaeIII. 200 ng of the resulting digestion products were mixed with 60 pmoles each of phosphorylated synthetic oligonucleotides containing the model RBS. These complementary deoxynucleotides (#1= TTAAAAATTAAGGAGG: #2=AATTCCTCCTTAATTTTTAA) were synthesized on solid support using the phosphite methodology (Matteucci, M. D. and Caruthers, M. H. "Synthesis of Deoxyoligonucleotides on a Polymer Support" J. Am. Chem. Soc. (1983) 103:3185–3191). Synthesis was initiated with 1 μmole of the 3'-terminal nucleoside attached to a controlled pore glass support (Pierce CPG/long chain alkylamine resin). This mixture was incubated with T4 DNA ligase at 15° C. for 18 hours, and the ligated molecules were digested with BglII and EcoRI and separated on a 5% polyacrylamide gel. The 270 bp ligation product was recovered from the gel, mixed with gel purified pRC2 vector that had been digested with BglII and EcoRI, and incubated with T4 DNA ligase at 15° for 15 hours. The ligation mixture was used to transform strain RR1 (pRK248cIts). Transformants selected on ampicillin-containing medium were screened by restriction analysis of the isolated plasmid DNA. The expected plasmid construction, pRC23, was confirmed by further restriction enzyme digestions and by DNA sequence analysis across the EcoRI junction. Plasmid pRC23 contains a unique EcoRI site at the 3' end of the RBS, into which genes containing an ATG at the 5' end can be inserted.

For the construction of pEV-vrf2, pRC23 was digested with EcoRI and Hind III and the linearized vector isolated by preparative agarose gel electrophoresis. Two complementary deoxynucleotides (#3= AATTAATATGAATAGAATTCGGATCCATCGATA, #4=AGCTTATCGATGGATCCGAATTCTATTCATATT) were synthesized (supra), combined and heated to 58° C. for 5 minutes in 150 mM NaCl, and cooled slowly to allow annealing. 0.1 pmoles of the synthetic duplexes were added to 0.07 pmoles of the pRC23/EcoRI-HindIII vector and incubated with T4 DNA ligase at 15° C. for 15 hours. Strain RR1 (pRK248cIts) was transformed with the ligation products, and ampicillin—resistant transformants were screened by restriction endonuclease cleavage analysis to identify pEV-vrf2, the expected construction of which was confirmed by DNA sequence analysis. Plasmid pEV-vrf2 contains restriction sites (EcoRI, BamHI, ClaI, and HindIII) located downstream from an appropriately positioned initiation codon—RBS. Hence, appropriately positioned coding region sequences inserted into these restriction sites will be expressed under control of the $P_L$ promoter yielding the corresponding protein with 2–9 extra amino-terminal amino acids. Site directed mutagenesis can be used to remove these extraneous amino acids, as well as to re-orient inappropriately positioned (i.e. the reading frame is not correct) coding sequences.

Synthetic oligonucleotides 5'-GGGCGTTATTCAGGACGAATTCGTA-3' and 5'-ATTGCTCA GG AACATATTAATCC-3' used above were synthesized on an Applied Biosystems model 380A DNA synthesizer. Diisopropyl phosphoramidites were used as the active nucleotidyl component for coupling to the support. See Beacage and Caruthers. Tetrahedron Lett. 22, 1859–1862 (1981). Synthesis on the support was carried out at 0.5 mmol level using a CPG resin with the 3' nucleotide attached to the resin as described by Matteucci and Caruthers, J. Am. Chem. Soc. 103, 3185–3189 (1981). The synthetic cycle was essentially the same as provided by the manufacturer, however, 2% dichloroacetic acid was used in place of 3% trichloroacetic acid as the detritylating reagent. Synthesized oligonucleotides were isolated on 20% polyacrylamide sequencing gels. Isolated oligonucleotides cut out from the gel were eluted in gel elution buffer and desalted on $C_{18}$ reverse-phase columns.

With the recombinant DNA thus obtained, living cells may be transformed to amplify the cloned cDNA or to produce IL-1 polypeptide.

Suitable eucaryotic host organisms, which may be employed for production of IL-1, include vertebra, yeast and the like. For instance, monkey cells, e.g. CV-1 cells, transformed by a replication origin defective mutant of SV-40 and expressing the SV-40 large T antigen (COS cells) as discussed by Gluzman (Cell 23, 175–182, 1981), mouse derived cells described by Ohno and Taniguchi (Nucleic Acids Research 10, 967–977 (1982)), and yeast host—vector systems which have been utilized for the expression of interferon genes, discussed by Hitzman et al. (Nature, 293, 717–722 (1981)) may be utilized. In addition, it is possible to use insect cells such as described by Smith et al. (Mol. Cell. Biol. 3, 2156–2165, 1983). Suitable procaryotic host organisms include *Escherichia coli, Bacillus subtilis* and the like. For amplification of DNA in host organisms, it may be preferred to use *E. coli* as a host, however other hosts can also be employed.

Suitable vectors used for *E. coli* include EK type plasmid vectors (stringent type): pSC101, pRK353, pRK646, pRK248, pDF41 etc., EK type plasmid vectors (relaxed type): ColEI, pVH51, pAC105, RSF2124, pCR1, pMB9, pBR313, pBR322, pBR324, pBR325, pBR327, pBR328, pKY2289, pKY2700, pKN80, pKC7, pKB158, pMK2004, pACYC1, pACYC184, dul etc. λ gt type phage vectors: λ gt, λc, λ gt, λ.B, λ WES, λc, λ gt, λB, λWES, λC, λWES, λB, λ ZJvir., λB', λALO, λB, λWES, Ts622, λDam etc. In general pBR322 has been frequently used as a vector for *E. coli*.

Transformation of the host cell with the recombinant DNA may be carried out by conventionally used methods as follows:

Where the host is prokaryotic such as *E. coli*, competent cells which are capable of DNA uptake are prepared from cells harvested during the exponential growth phase and subsequently treated by the $CaCl_2$-method by well known procedures. When $MgCl_2$ or RbCl exists in the transformation reaction medium, the transformation efficiency increases. Transformation can be also performed after forming a protoplast of the host cell.

Where the host used is eucaryotic, transfection methods of DNA as calcium phosphate-precipitates, conventional mechanical procedures such as microinjection, insertion of a plasmid encapsulated in red blood cell hosts or in liposomes, treatment of cells with agents such as lysophosphatidylcholine, or use of virus vectors, or the like may be used.

However, various other microbial strains are useful, including known *E. coli* strains such as *E. coli* B. *E. coli* X 1776 (ATCC No. 31537) and *E. coli* W 3310 (ATCC No. 27325), and most preferably *E. coli* RR1 or other microbial strains such as MC 1061, many of which are deposited and available from depository institutions, such as the American Type Culture Collection (ATCC)—cf. the ATCC catalogue listing. See also German Offenlegungsschrift 2644432. These other microorganisms include, for example, Bacilli such as *Bacillus subtilis* and enterobacteriaceae among which can be mentioned as examples *Salmonella typhimurium* and *Serratia marescens*, utilizing plasmids that can replicate and express heterologous gene sequences therein.

As examples, the beta lactamase and lactose promoter systems have been advantageously used to initiate and sustain microbial production of heterologous polypeptides. Details relating to the make-up and construction of these promoter systems have been published by Chang et al., *Nature* 275, 617 (1978) and Itakura et al., *Science* 198, 1056 (1977), which are hereby incorporated by reference. More recently, a system based upon tryptophan, the so-called trp promoter system, has been developed. Details relating to the make-up and construction of this system have been published by Goeddel et al., *Nucleic Acids Research* 8, 4057 (1980). Numerous other microbial promoters have been discovered and utilized and details concerning their nucleotide sequences, enabling a skilled worker to ligate them functionally within plasmid vectors, have been published—see, e.g., Siebenlist et al., *Cell* 20, 269 (1980).

The expression system hereof may also employ the plasmid YRp7, which is capable of selection and replication in both *E. coli* and the yeast, *Saccharomyces cerevisiae*. A useful strain is RH218 deposited at the American Type Culture Collection without restriction (ATCC No. 44076). However, it will be understood that any *Saccharomyces cerevisiae* strain containing a mutation which makes the cell trp1 should be an effective environment for expression of the plasmid containing the expression system. An example of another strain which could be used is pep4-1. This tryptophan auxotroph strain also has a point mutation in the TRP1 gene.

The experience with expression of mouse IL-1 cDNA in *E. coli* suggests that the carboxy-terminal portion of the human IL-1 precursor should possess IL-1 biological activity. Clone phil #7 described above, contains the coding information for the carboxy-terminal 163 amino acids of the human IL-1 precursor. There is an Alu I restriction endonuclease cleavage site near the 5' end of the phil #7 insert (see FIG. 2A) within the codon for the ninth amino acid (that is, the $153^{rd}$ amino acid from the carboxy-terminal end of the precursor). The next down-stream Alu I site is in the 3' non-coding region (that is, past the termination codon) ~600 bp away. This ~600 bp Alu I fragment containing the sequences coding for the carboxy-terminal 154 amino acids of the human IL-1 precursor, was isolated from phil #7 and inserted into the BamHI site of an *E. coli* expression plasmid (as seen in FIG. 4) in the following manner. Using standard methods, the insert from clone phil #7 was digested with Alu I, and phosphorylated BamHI linkers (CGGATCCG New England Biolabs, Catalog 1021) were ligated to the Alu I cut insert using T4DNA ligase. The ligase was heat-inactivated and the mixture was treated with BamHI to remove excess linkers and to generate cohesive termini. This mixture was electrophoresed on a polyacrylamide gel and the ~600 bp fragment was isolated. Plasmid pEV-vrf2 was digested with BamHI and the linearized vector was recovered following agarose gel electrophoresis. The ~600 bp fragment and the BamHI cut vector were ligated together, and used to transform *E. coli* strain MC 1061 (Casadaban and Cohen J. Mol. Biol. 138, 179–207, 1980) containing the compatible plasmid pRK248cIts (Bernard and Helinski, Meth. Enzym. 68, 482–492, 1979) using selection for ampicillin resistance. Bacterial clones were screened by restriction endonuclease digestion analysis to identify a plasmid phil #1-154* containing the insert in the correct orientation. Plasmid phil #1-154* was partially sequenced to verify that its structure was correct. Bacteria containing phil #1-154* or the parental plasmid pEV-vrf2 were grown in M9 media containing ampicillin at 30° C. until the $A_{550}$ reached 0.7, at which time the cultures were shifted to 42° C. for 3 hours. The bacteria from 1 ml of culture were recovered by centrifugation and solubilized in 50 micro liters of 7M guanidine hydrochloride. These crude bacterial extracts were examined for IL-1 activity in the murine thymocyte proliferation assay (Mizel et al. supra). Extracts of bacteria containing only pEV-vrf2 did not stimulate in the assay above background levels. Extracts of bacteria containing phil #1-154* contained 32,000 units of IL-1 activity/ml of guanidine HCl solution. Assuming a specific activity of $6 \times 10^6$ units per mg, this is equivalent to at least 0.3 mg of IL-1 protein per liter of bacterial culture.

Figure 5B:
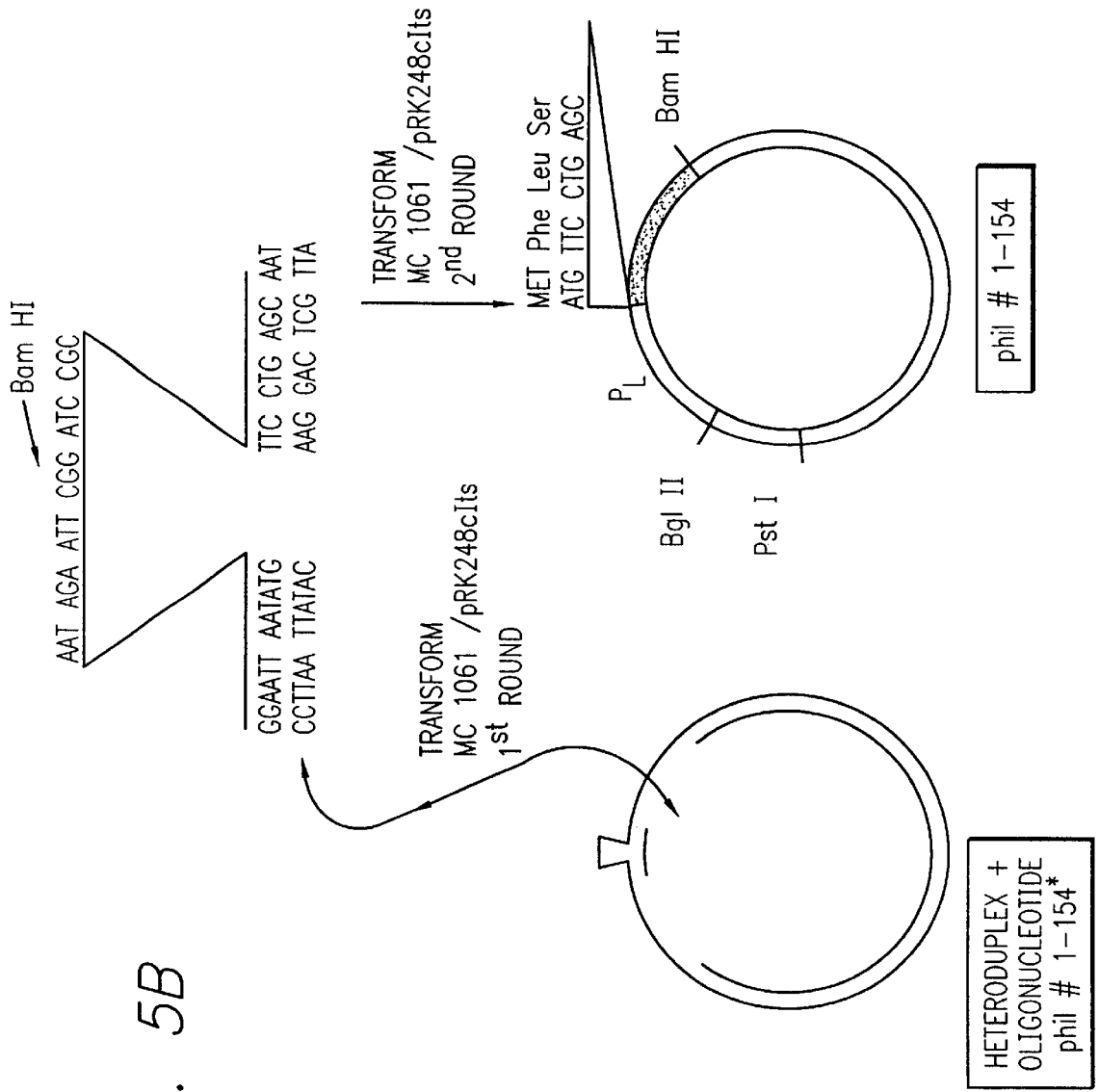

The protein encoded by expression plasmid phil #1-154* contains, in addition to the initiator methionine, 6 extraneous amino acids at its amino terminus. These were removed by site directed mutagenisis as follows:

1–2 µg of plasmid phil#1-154* was subjected to restriction endonuclease digestion in two separate reactions. In one reaction, 1–2 units of both Bgl II and Bam HI created a linearized plasmid with a gap (see FIG. 5), and in the other reaction, 1 unit of Pst I generated a linearized plasmid. Pst I treatment was followed by treatment with 1 unit of Klenow fragment of *E. coli* DNA polymerase I. These opened plasmids were purified by electrophoresis through a 0.7% aparose gel and recovered by ethanol precipitation. Each plasmid was resuspended in 5 µl $H_2O$. A 1 µl aliquot was taken from each and was combined with 50 ng of phosphorylated synthetic oligonucleotide: 5'-P-ATTGCTCAGGAACATATTATTCC-OH-3' in a 12 µl reaction containing 12 mM Tris.HCl, pH 7.5, 9 mM $MgCl_2$, 200 mM NaCl and 20 µl beta mercaptoethanol. The reaction was heated to 100° C. for 3' to denature the opened plasmids, and the annealing of the oligonucleotide was permitted by gradually cooling the reaction at 23° C. for 30', followed by 4° C. for 30' and 0° C. for 10'. This resulted in the formation of a heteroduplex form of phil #1-154* with the oligonucleotide annealed to the single-stranded region.

The single-stranded region was made double-stranded and the plasmid was ligated in a 20 µl reaction volume of 75 µM dATP, 75 µM dTTP, 75 µM dCTP, 75 µM dGTP, 500 µM ATP, 2–3 units of the Klenow fragment of *E. coli* DNA polymerase I and 1 unit of $T_4$ DNA ligase. This reaction proceeded at 15° C. for 12–16 hours. Plasmid DNA was recovered by ethanol precipitation and resuspended in 10 µl $H_2O$. A 5 µl aliquot was used to transform the MC1061 strain of *E. coli* containing the compatible plasmid pRk248cIts to ampicillin resistance. Ampicillin resistant transformants were screened for the new plasmid phil #1-154 in the phil #1-154* background by recovering plasmid DNA from individual transformants and performing Bgl II/Bam HI restriction digestion on this plasmid DNA preparation. Plasmid DNA which contained phil #1-154 was used in a second round of MC 1061 pRK248cIts transformation to separate phil #1-154 and phil #1-154*. Transformants containing only phil #1-154 were recovered and an individual *E. coli* colony was used for the production of the phil #1-154 protein as described above.

Purification of Recombinant Human Interleukin-1

Like many other recombinant proteins (see Williams, D. C. et al. *Science* (1982) 215:687–688; Lacal, J. C. et al. *Proc. Natl. Acad. Sci.* (1984) 81:5305–5309), human interleukin-1 aggregates into insoluble cytoplasmic "inclusion bodies" within *E. coli*. Hence the purification of recombinant human IL-1 begins with the isolation of these "inclusion bodies" (see Lacal et al., supra).

E. coli cell paste (1 g) was suspended in 5 ml of 1 mM phenylmethylsulfonyl fluoride in buffer A (30 mM Tris-HCl, pH 8, in 5 mM EDTA) and the cells were sonicated six times for a total of 3 minutes using a Sonifier cell disrupter Model 350 (Branson Sonic Power Co.). The cell lysate was centrifuged for 30 minutes at 30,000×g to separate the insoluble fraction. The particulate fraction (which contains most of IL-1 activity) was sequentially washed with 5 ml each of 1) buffer A, 2) 1% Triton X-100 in buffer A and 3) 1.75 M guanidine HCl. After each wash, the particulate fraction was pelleted by centrifugation at 30,000×g for 20 minutes. IL-1 activity was solubilized from the remaining particulate fraction by 3 ml of 5 M guanidine HCl, followed by centriguation at 30,000×g for 30 minutes. Up to this step, all procedures were carried out at 4° C. The solubilized IL-1 protein was purified to homogeneity by gel filtration chromatography on Sephacryl S-200 or Sephadex G-75 (Pharmacia Fine Chemicals. Piscataway, N.J.) equilibrated and eluted with 5M guanidine HCl. The purified 1–154* IL-1 behaved as a single polypeptide on SDS polyacrylamide gels (Laemmli, U. K. *Nature* (1970) 227:680–685). When submitted for amino acid compositional analysis and amino-terminal sequence analysis, the expected results were obtained, thus verifying the purity and identity of the protein. In similar fashion *E. coli* transformed with phil #1-154 were used to produce 1–154 protein which was purified as above.

Experiments with the expression products of deletion mutants of the mouse IL-1 gene has provided a basis for determining the minimum sequence which provides a bioactive protein from the carboxy-terminal of the mouse IL-1 precursor. The results are summarized below in Table I.

TABLE I

Activity of Mouse IL-1 Deletion Mutants

| Protein[1] | Activity[2] |
|---|---|
| 1-156 | $6 \times 10^6$ |
| 17-156 | $6 \times 10^6$ |
| 30-156 | 0 |
| 1-143,156 | 0 |
| 17-143,156 | 0 |
| 30-143,156 | 0 |

[1]in this nomenclature, protein 1-156 contains the carboxy-terminal 156 amino acids of the mouse IL-1 precursor. All the deletion mutants are defined relative to this molecule, hence protein 17-156 is missing the amino-terminal 16 amino acids compared to protein 1-156; protein 1-143, 156 is missing amino acids 144-155 compared to protein 1-156.
[2]in the thymocyte proliferation assay, units per mg protein.

As seen in Table I the sequence proximal to the carboxy-terminus is needed for activity. A minimum of about 139 amino acids is apparently required to maintain activity as the 17–156 exhibits high activity, whereas deletion of an additional thirteen amino acids at the amino-terminus of this fragment destroys the activity. Thus, by analogy to the mouse molecule data it is believed that the sequence encompassing the carboxy-terminal 139 amino acids of the human IL-1 precursor is the minimum fragment exhibiting IL-1 activity. This would correspond to positions 132–271 of the human IL-1 precursor protein sequence set forth in FIG. 2B. Therefore, one aspect of the present invention relates to peptides exhibiting human IL-1 activity which encompass the aforesaid minimum carboxy-terminal sequence.

The purified recombinant human IL-1 peptides encompassing the sequence needed for biological activity can be employed in a manner known per se to stimulate the immune system of a host subject, such as, for example, by improving host defense response to pathogens, by acting as a vaccine adjuvant and by enhancing host defense against neoplastic diseases. Other clinical uses identified for human IL-1 in the art include promotion of wound healing via stimulation of fibroblast proliferation and improvement of the recovery of critically ill, protein-malnourished patients.

Purified IL-1 peptides prepared in accordance with this invention may be administered to warm blooded mammals for the clinical uses indicated above. The administration may be by any conventional method such as by parenteral application either intravenously, subcutaneously or intramuscularly. Obviously, the required dosage will vary with the particular condition being treated, the severity of the condition, the duration of the treatment and the method for administration. A suitable dosage form for pharmaceutical use may be obtained from sterile filtered, lyophilized IL-1 peptide reconstituted prior to use in a conventional manner. It is also within the skill of the art to introduce buffers, stabilizers, bacteriostats and other excipients and additives conventionally employed in pharmaceutical parenteral dosage forms.

What is claimed is:

1. An isolated DNA fragment encoding an interleukin-1α polypeptide, wherein said DNA fragment encodes the following amino acid sequence:

Met Phe Leu Ser Asn Val Lys Tyr Asn Phe MET Arg Ile Ile Lys Tyr Glu Phe Ile Leu Asn Asp Ala Leu Asn Gln Ser Ile Ile Arg Ala Asn Asp Gln Tyr Leu Thr Ala Ala Ala Leu His Asn Leu Asp Glu Ala Val Lys Phe Asp MET Gly Ala Tyr LyS Ser Ser Lys Asp Asp Ala Lys Ile Thr Val Ile Leu Arg Ile Ser Lys Thr Gln Leu Tyr Val Thr Ala Gln Asp Glu Asp Gln Pro Val Leu Leu Lys Glu MET Pro Glu Ile Pro Lys Thr Ile Thr Gly Ser Glu Thr Asn Leu Leu Phe Phe Trp Glu Thr His Gly Thr Lys Asn Tyr Phe Thr Ser Val Ala His Pro Asn Leu Phe Ile Ala Thr Lys Gln Asp Tyr Trp Val Cys Leu Ala Gly Gly Pro Pro Ser Ile Thr Asp Phe Gln Ile Leu Glu Asn Gln Ala and the last nucleotide of the codon encoding the last amino acid of the sequence is immediately followed by a translational stop signal.

2. An isolated DNA fragment encoding an interleukin-1α polypeptide having interleukin-1 activity, wherein said DNA fragment encodes a polypeptide comprising the minimum sequence needed for interleukin-1 activity, said minimum sequence corresponding to positions 132 to 271 of a human interleukin-1α precursor polypeptide and the last nucleotide of the codon encoding amino acid 271 of the sequence is immediately followed by a translational stop signal.

3. The isolated DNA fragment of claim 2, wherein said minimum sequence corresponding to positions 132 to 271 of the human interleukin-1α precursor polypeptide is:

132

Tyr Glu Phe Ile Leu Asn Asp Ala Leu Asn Gln Ser Ile Ile Arg Ala Asn Asp Gln Tyr Leu Thr Ala Ala Ala Leu His Asn Leu Asp Glu Ala Val Lys Phe Asp MET Gly Ala Tyr Lys Ser Ser Lys Asp Asp Ala Lys Ile Thr Val Ile Leu Arg Ile Ser Lys Thr Gln Leu Tyr Val Thr Ala Gln Asp Glu Asp Gln Pro Val Leu Leu Lys Glu MET Pro Glu Ile Pro Lys Thr Ile Thr Gly Ser Glu Thr Asn Leu Leu Phe Phe Trp Glu Thr His Gly Thr Lys Asn Tyr Phe Thr Ser Val Ala His Pro Asn Leu Phe Ile Ala Thr Lys Gln Asp Tyr Trp Val Cys Leu Ala Gly Gly Pro Pro Ser Ile Thr Asp Phe Gln Ile Leu Glu Asn Gln Ala

271.

4. An isolated DNA fragment encoding an interleukin-1α polypeptide having interleukin-1 activity, wherein said DNA fragment encodes the following amino acid sequence:

1
MET Ala Lys Val Pro Asp MET Phe Glu Asp Leu Lys Asn
Cys Tyr Ser Glu Asn Glu Glu Asp Ser Ser Ser Ile Asp
His Leu Ser Leu Asn Gln Lys Ser Phe Tyr His Val Ser
Tyr Gly Pro Leu His Glu Gly Cys MET Asp Gln Ser Val
Ser Leu Ser Ile Ser Glu Thr Ser Lys Thr Ser Lys Leu
Thr Phe Lys Glu Ser MET Val Val Val Ala Thr Asn Gly
Lys Val Leu Lys Lys Arg Arg Leu Ser Leu Ser Gln Ser
Ile Thr Asp Asp Asp Leu Glu Ala Ile Ala Asn Asp Ser
Glu Glu Glu Ile Ile Lys Pro Arg Ser Ala Pro Phe Ser Phe
Leu Ser Asn Val Lys Tyr Asn Phe MET Arg Ile Ile Lys
Tyr Glu Phe Ile Leu Asn Asp Ala Leu Asn Gln Ser Ile
Ile Arg Ala Asn Asp Gln Tyr Leu Thr Ala Ala Ala Leu
His Asn Leu Asp Glu Ala Val Lys Phe Asp MET Gly
Ala Tyr Lys Ser Ser Lys Asp Asp Ala Lys Ile Thr Val
Ile Leu Arg Ile Ser Lys Thr Gln Leu Tyr Val Thr Ala Gln
Asp Glu Asp Gln Pro Val Leu Leu Lys Glu MET Pro
Glu Ile Pro Lys Thr Ile Thr Gly Ser Glu Thr Asn Leu
Leu Phe Phe Trp Glu Thr His Gly Thr Lys Asn Tyr Phe
Thr Ser Val Ala His Pro Asn Leu Phe Ile Ala Thr Lys
Gln Asp Tyr Trp Val Cys Leu Ala Gly Gly Pro Pro Ser
Ile Thr Asp Phe Gln Ile Leu Glu Asn Gln Ala
271
and the last nucleotide of the codon encoding amino acid 271 of the sequence is immediately followed by a translational stop signal.

5. An isolated DNA fragment encoding an interleukin-1α polypeptide having human interleukin-1 activity and having the nucleotide sequence of FIG. 2A.

6. An isolated DNA fragment encoding an interleukin-1α polypeptide having human interleukin-1 activity and having the nucleotide sequence of FIG. 2B.

7. A recombinant DNA which comprises an isolated DNA fragment capable of expressing a polypeptide having the following amino acid sequence:

Met Phe Leu Ser Asn Val Lys Tyr Asn Phe MET Arg Ile
Ile Lys Tyr Glu Phe Ile Leu Asn Asp Ala Leu Asn Gln
Ser Ile Ile Arg Ala Asn Asp Gln Tyr Leu Thr Ala Ala
Ala Leu His Asn Leu Asp Glu Ala Val Lys Phe Asp
MET Gly Ala Tyr Lys Ser Ser Lys Asp Asp Ala Lys Ile
Thr Val Ile Leu Arg Ile Ser Lys Thr Gln Leu Tyr Val Thr
Ala Gln Asp Glu Asp Gln Pro Val Leu Leu Lys Glu
MET Pro Glu Ile Pro Lys Thr Ile Thr Gly Ser Glu Thr
Asn Leu Leu Phe Phe Trp Glu Thr His Gly Thr Lys Asn
Tyr Phe Thr Ser Val Ala His Pro Asn Leu Phe Ile Ala
Thr Lys Gln Asp Tyr Trp Val Cys Leu Ala Gly Gly Pro
Pro Ser Ile Thr Asp Phe Gln Ile Leu Glu Asn Gln Ala.

8. The recombinant DNA of claim 7, wherein said vector DNA comprises a phage lambda promoter.

9. The recombinant DNA of claim 7, wherein said vector DNA comprises a Trp promoter.

10. The recombinant DNA of claim 7, wherein said vector DNA comprises a SV 40 promoter.

11. A recombinant DNA which comprises an isolated DNA fragment capable of expressing a polypeptide having interleukin-1 activity and comprising the minimum sequence needed for interleukin-1 activity, said minimum sequence corresponding to positions 132 to 271 of a human interleukin-1α precursor polypeptide.

12. A recombinant DNA which comprises an isolated DNA fragment capable of expressing a polypeptide having the following amino acid sequence:

1
MET Ala Lys Val Pro Asp MET Phe Glu Asp Leu Lys Asn
Cys Tyr Ser Glu Asn Glu Glu Asp Ser Ser Ser Ile Asp
His Leu Ser Leu Asn Gln Lys Ser Phe Tyr His Val Ser
Tyr Gly Pro Leu His Glu Gly Cys MET Asp Gln Ser Val
Ser Leu Ser Ile Ser Glu Thr Ser Lys Thr Ser Lys Leu
Thr Phe Lys Glu Ser MET Val Val Val Ala Thr Asn Gly
Lys Val Leu Lys Lys Arg Arg Leu Ser Leu Ser Gln Ser
Ile Thr Asp Asp Asp Leu Glu Ala Ile Ala Asn Asp Ser
Glu Glu Glu Ile Ile Lys Pro Arg Ser Ala Pro Phe Ser Phe
Leu Ser Asn Val Lys Tyr Asn Phe MET Arg Ile Ile Lys
Tyr Glu Phe Ile Leu Asn Asp Ala Leu Asn Gln Ser Ile
Ile Arg Ala Asn Asp Gln Tyr Leu Thr Ala Ala Ala Leu
His Asn Leu Asp Glu Ala Val Lys Phe Asp MET Gly
Ala Tyr Lys Ser Ser Lys Asp Asp Ala Lys Ile Thr Val
Ile Leu Arg Ile Ser Lys Thr Gln Leu Tyr Val Thr Ala Gln
Asp Glu Asp Gln Pro Val Leu Leu Lys Glu MET Pro
Glu Ile Pro Lys Thr Ile Thr Gly Ser Glu Thr Asn Leu
Leu Phe Phe Trp Glu Thr His Gly Thr Lys Asn Tyr Phe
Thr Ser Val Ala His Pro Asn Leu Phe Ile Ala Thr Lys
Gln Asp Tyr Trp Val Cys Leu Ala Gly Gly Pro Pro Ser
Ile Thr Asp Phe Gln Ile Leu Glu Asn Gln Ala
271.

13. A eucaryotic or procaryotic cell transformed with a recombinant DNA capable of expressing a polypeptide having the following amino acid sequence:

Met Phe Leu Ser Asn Val Lys Tyr Asn Phe MET Arg Ile
Ile Lys Tyr Glu Phe Ile Leu Asn Asp Ala Leu Asn Gln
Ser Ile Ile Arg Ala Asn Asp Gln Tyr Leu Thr Ala Ala
Ala Leu His Asn Leu Asp Glu Ala Val Lys Phe Asp
MET Gly Ala Tyr Lys Ser Ser Lys Asp Asp Ala Lys Ile
Thr Val Ile Leu Arg Ile Ser Lys Thr Gln Leu Tyr Val Thr
Ala Gln Asp Glu Asp Gln Pro Val Leu Leu Lys Glu
MET Pro Glu Ile Pro Lys Thr Ile Thr Gly Ser Glu Thr
Asn Leu Leu Phe Phe Trp Glu Thr His Gly Thr Lys Asn
Tyr Phe Thr Ser Val Ala His Pro Asn Leu Phe Ile Ala
Thr Lys Gln Asp Tyr Trp Val Cys Leu Ala Gly Gly Pro
Pro Ser Ile Thr Asp Phe Gln Ile Leu Glu Asn Gln Ala.

14. The transformed cell of claim 13, which is a prokaryotic cell belonging to the genus Escherichia.

15. A eucaryotic or procaryotic cell transformed with a recombinant DNA capable of expressing a polypeptide having interleukin-1 activity and comprising the minimum sequence needed for interleukin-1 activity, said minimum sequence corresponding to positions 132 to 271 of a human interleukin-1α precursor polypeptide.

16. A eucaryotic or procaryotic cell transformed with a recombinant DNA capable of expressing a polypeptide having the following amino acid sequence:

1
MET Ala Lys Val Pro Asp MET Phe Glu Asp Leu Lys Asn
Cys Tyr Ser Glu Asn Glu Glu Asp Ser Ser Ser Ile Asp
His Leu Ser Leu Asn Gln Lys Ser Phe Tyr His Val Ser
Tyr Gly Pro Leu His Glu Gly Cys MET Asp Gln Ser Val
Ser Leu Ser Ile Ser Glu Thr Ser Lys Thr Ser Lys Leu
Thr Phe Lys Glu Ser MET Val Val Val Ala Thr Asn Gly
Lys Val Leu Lys Lys Arg Arg Leu Ser Leu Ser Gln Ser
Ile Thr Asp Asp Asp Leu Glu Ala Ile Ala Asn Asp Ser
Glu Glu Glu Ile Ile Lys Pro Arg Ser Ala Pro Phe Ser Phe
Leu Ser Asn Val Lys Tyr Asn Phe MET Arg Ile Ile Lys
Tyr Glu Phe Ile Leu Asn Asp Ala Leu Asn Gln Ser Ile
Ile Arg Ala Asn Asp Gln Tyr Leu Thr Ala Ala Ala Leu
His Asn Leu Asp Glu Ala Val Lys Phe Asp MET Gly
Ala Tyr Lys Ser Ser Lys Asp Asp Ala Lys Ile Thr Val
Ile Leu Arg Ile Ser Lys Thr Gln Leu Tyr Val Thr Ala Gln
Asp Glu Asp Gln Pro Val Leu Leu Lys Glu MET Pro
Glu Ile Pro Lys Thr Ile Thr Gly Ser Glu Thr Asn Leu
Leu Phe Phe Trp Glu Thr His Gly Thr Lys Asn Tyr Phe
Thr Ser Val Ala His Pro Asn Leu Phe Ile Ala Thr Lys

Gln Asp Tyr Trp Val Cys Leu Ala Gly Gly Pro Pro Ser Ile Thr Asp Phe Gln Ile Leu Glu Asn Gln Ala.

271.

17. A method for producing an interleukin-1α polypeptide which comprises culturing a eucaryotic or procaryotic cell in culture medium, said cell being transformed with a recombinant DNA capable of expressing a polypeptide having the following amino acid sequence:

Met Phe Leu Ser Asn Val Lys Tyr Asn Phe MET Arg Ile Ile Lys Tyr Glu Phe Ile Leu Asn Asp Ala Leu Asn Gln Ser Ile Ile Arg Ala Asn Asp Gln Tyr Leu Thr Ala Ala Ala Leu His Asn Leu Asp Glu Ala Val Lys Phe Asp MET Gly Ala Tyr Lys Ser Ser Lys Asp Asp Ala Lys Ile Thr Val Ile Leu Arg Ile Ser Lys Thr Gln Leu Tyr Val Thr Ala Gln Asp Glu Asp Gln Pro Val Leu Leu Lys Glu MET Pro Glu Ile Pro Lys Thr Ile Thr Gly Ser Glu Thr Asn Leu Leu Phe Phe Trp Glu Thr His Gly Thr Lys Asn Tyr Phe Thr Ser Val Ala His Pro Asn Leu Phe Ile Ala Thr Lys Gln Asp Tyr Trp Val Cys Leu Ala Gly Gly Pro Pro Ser Ile Thr Asp Phe Gln Ile Leu Glu Asn Gln Ala.

18. A method for producing an interleukin-1α polypeptide which comprises culturing a eucaryotic or procaryotic cell in culture medium, said cell being transformed with a recombinant DNA capable of expressing a polypeptide having interleukin-1 activity and comprising the minimum sequence needed for interleukin-1 activity, said minimum sequence corresponding to positions 132 to 271 of a human interleukin-1α precursor polypeptide.

19. The method of claim 18, wherein said DNA fragment is for the precursor of human interleukin-1α, said cell is a eucaryotic cell and said biologically active form of said human interleukin-1α is obtained by post-expression modification.

20. The method of claim 19, wherein a heterogeneous population of biologically active forms of human interleukin-1α varying at the amino terminus is formed.

21. A method for producing an interleukin-1α polypeptide which comprises culturing a eucaryotic or procaryotic cell in culture medium, said cell being transformed with a recombinant DNA capable of expressing a polypeptide having the following amino acid sequence:

MET Ala Lys Val Pro Asp MET Phe Glu Asp Leu Lys Asn Cys Tyr Ser Glu Asn Glu Glu Asp Ser Ser Ser Ile Asp His Leu Ser Leu Asn Gln Lys Ser Phe Tyr His Val Ser Tyr Gly Pro Leu His Glu Gly Cys MET Asp Gln Ser Val Ser Leu Ser Ile Ser Glu Thr Ser Lys Thr Ser Lys Leu Thr Phe Lys Glu Ser MET Val Val Val Ala Thr Asn Gly Lys Val Leu Lys Lys Arg Arg Leu Ser Leu Ser Gln Ser Ile Thr Asp Asp Asp Leu Glu Ala Ile Ala Asn Asp Ser Glu Glu Glu Ile Ile Lys Pro Arg Ser Ala Pro Phe Ser Phe Leu Ser Asn Val Lys Tyr Asn Phe MET Arg Ile Ile Lys Tyr Glu Phe Ile Leu Asn Asp Ala Leu Asn Gln Ser Ile Ile Arg Ala Asn Asp Gln Tyr Leu Thr Ala Ala Ala Leu His Asn Leu Asp Glu Ala Val Lys Phe Asp MET Gly Ala Tyr Lys Ser Ser Lys Asp Asp Ala Lys Ile Thr Val Ile Leu Arg Ile Ser Lys Thr Gln Leu Tyr Val Thr Ala Gln Asp Glu Asp Gln Pro Val Leu Leu Lys Glu MET Pro Glu Ile Pro Lys Thr Ile Thr Gly Ser Glu Thr Asn Leu Leu Phe Phe Trp Glu Thr His Gly Thr Lys Asn Tyr Phe Thr Ser Val Ala His Pro Asn Leu Phe Ile Ala Thr Lys Gln Asp Tyr Trp Val Cys Leu Ala Gly Gly Pro Pro Ser Ile Thr Asp Phe Gln Ile Leu Glu Asn Gln Ala.

* * * * *